(12) United States Patent
Welch et al.

(10) Patent No.: US 11,633,136 B2
(45) Date of Patent: Apr. 25, 2023

(54) BODILY FLUID COLLECTION DEVICES AND RELATED METHODS

(71) Applicant: Tasso, Inc., Seattle, WA (US)

(72) Inventors: Emily Welch, Seattle, WA (US); Ellen Hayes, Seattle, WA (US); Erwin Berthier, Seattle, WA (US); Jake Myre, Seattle, WA (US); Ben Casavant, Seattle, WA (US); Chris Smith, Seattle, WA (US); Jared Andrew Salstrom, Lake Stevens, WA (US); Steven Henry Bietzer, Seattle, WA (US); William Peter Stiles, Bothell, WA (US)

(73) Assignee: Tasso, Inc., Seattle, WA (US)

( * ) Notice: Subject to any disclaimer, the term of this patent is extended or adjusted under 35 U.S.C. 154(b) by 0 days.

(21) Appl. No.: 17/681,558

(22) Filed: Feb. 25, 2022

(65) Prior Publication Data

US 2022/0273208 A1   Sep. 1, 2022

Related U.S. Application Data

(60) Provisional application No. 63/154,537, filed on Feb. 26, 2021.

(51) Int. Cl.
*A61B 5/151* (2006.01)
*A61B 5/15* (2006.01)

(52) U.S. Cl.
CPC .... *A61B 5/15117* (2013.01); *A61B 5/150221* (2013.01)

(58) Field of Classification Search
None
See application file for complete search history.

(56) References Cited

U.S. PATENT DOCUMENTS 5,196,025 A     3/1993  Ranalletta et al.
5,314,441 A  *  5/1994  Cusack ............ A61B 5/150022
                                                606/182
(Continued)

FOREIGN PATENT DOCUMENTS

CN       106236112        12/2016
WO    WO-0100090 A1  *   1/2001  ....... A61B 5/150022
(Continued)

OTHER PUBLICATIONS

International Search Report and Written Opinion received for PCT Application No. PCT/US2022/018016; Applicant: Tasso, Inc., dated May 18, 2022, 8 pages.

(Continued)

*Primary Examiner* — Matthew Kremer
(74) *Attorney, Agent, or Firm* — Perkins Coie LLP

(57) ABSTRACT

Devices and methods for withdrawing bodily fluid from a subject are disclosed herein. In some embodiments, a handheld device can include a housing having an opening, a skin-piercing assembly, and an actuator coupled to the skin-piercing assembly. The skin-piercing assembly can include a casing, a drive member pivotably mounted within the casing and carrying a blade, and a biasing member coupling the drive member to the casing. The actuator can be movable relative to the housing from a first position to a second position. In the first position, the drive member can engage the casing to maintain the biasing member in a biased configuration. Movement of the actuator from the first position to the second position can disengage the drive member from the casing to permit the biasing member to drive the blade at least partially through and/or across the opening in the base.

17 Claims, 21 Drawing Sheets

(56) References Cited

U.S. PATENT DOCUMENTS

| | | | |
|---|---|---|---|
| 5,476,474 A | 12/1995 | Davis et al. | |
| 5,772,677 A | 6/1998 | Mawhirt et al. | |
| 6,010,519 A | 1/2000 | Mawhirt et al. | |
| 6,042,595 A | 3/2000 | Morita | |
| 6,221,089 B1 | 4/2001 | Mawhirt | |
| 6,264,619 B1 * | 7/2001 | Ferguson | A61B 5/150305 206/569 |
| 7,160,313 B2 | 1/2007 | Galloway et al. | |
| 7,316,698 B1 * | 1/2008 | Galloway | A61B 5/15111 600/583 |
| 7,452,365 B2 | 11/2008 | Galloway et al. | |
| 7,670,300 B2 | 3/2010 | Vreeke et al. | |
| 7,704,265 B2 | 4/2010 | Schraga | |
| 7,846,110 B2 | 12/2010 | Kloepfer et al. | |
| 7,879,058 B2 | 2/2011 | Ikeda | |
| 7,981,131 B2 | 7/2011 | Shi | |
| 7,998,161 B2 | 8/2011 | Shi | |
| 8,025,628 B2 | 9/2011 | Wong et al. | |
| 8,382,681 B2 | 2/2013 | Escutia et al. | |
| 8,454,642 B2 | 6/2013 | Schraga | |
| 8,512,367 B2 | 8/2013 | Robbins et al. | |
| 8,715,307 B2 | 5/2014 | Sun | |
| 8,821,412 B2 | 9/2014 | Gonzalez-Zugasti et al. | |
| 8,840,634 B2 | 9/2014 | Sun et al. | |
| 8,876,846 B2 | 11/2014 | Schraga | |
| 9,138,184 B2 | 9/2015 | Lum | |
| 9,220,447 B2 | 12/2015 | Richter et al. | |
| 9,724,031 B2 | 8/2017 | Yi et al. | |
| 9,839,384 B2 | 12/2017 | Escutia et al. | |
| 10,034,627 B2 | 7/2018 | Booker et al. | |
| 2008/0097502 A1 | 4/2008 | Winters-Hilt et al. | |
| 2008/0243159 A1 | 10/2008 | Schraga | |
| 2009/0287237 A1 | 11/2009 | Nicholls | |
| 2010/0010528 A1 * | 1/2010 | Shi | A61B 5/15113 606/182 |
| 2010/0023045 A1 | 1/2010 | Macho et al. | |
| 2015/0080929 A1 | 3/2015 | Yi et al. | |
| 2015/0209068 A1 | 7/2015 | Booker et al. | |
| 2016/0331292 A1 | 11/2016 | Leskowich et al. | |
| 2020/0085414 A1 | 3/2020 | Berthier et al. | |
| 2021/0059588 A1 | 3/2021 | Welch et al. | |

FOREIGN PATENT DOCUMENTS

| | | |
|---|---|---|
| WO | WO2002100253 | 12/2002 |
| WO | WO2020223710 | 11/2020 |
| WO | WO2021041881 | 3/2021 |

OTHER PUBLICATIONS

International Search Report and Written Opinion received for PCT Application No. PCT/US2020/048506; Applicant: Tasso, Inc., dated Nov. 13, 2020, 12 pages.

* cited by examiner

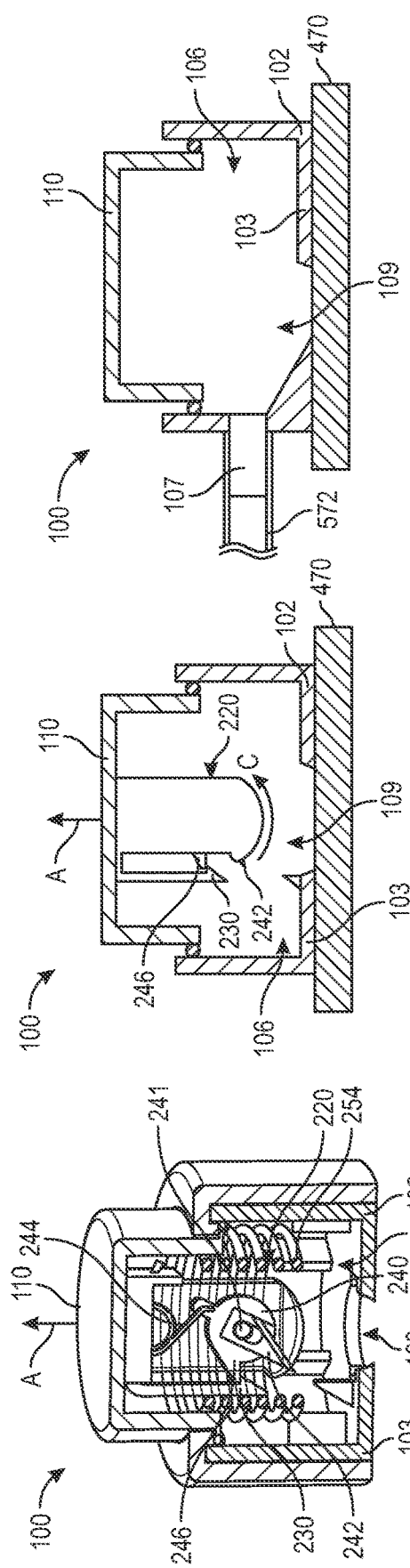
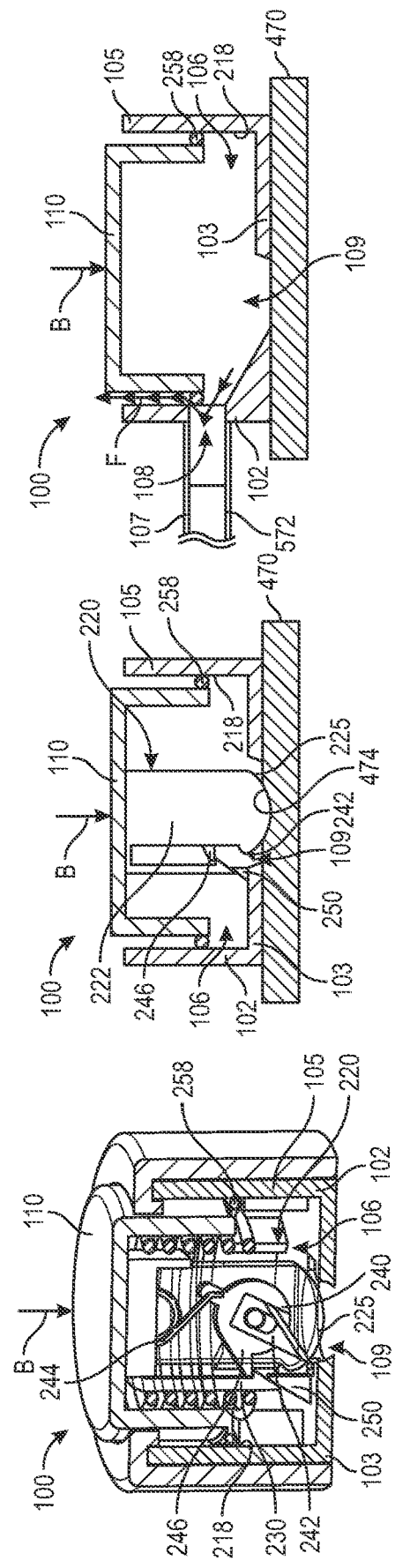

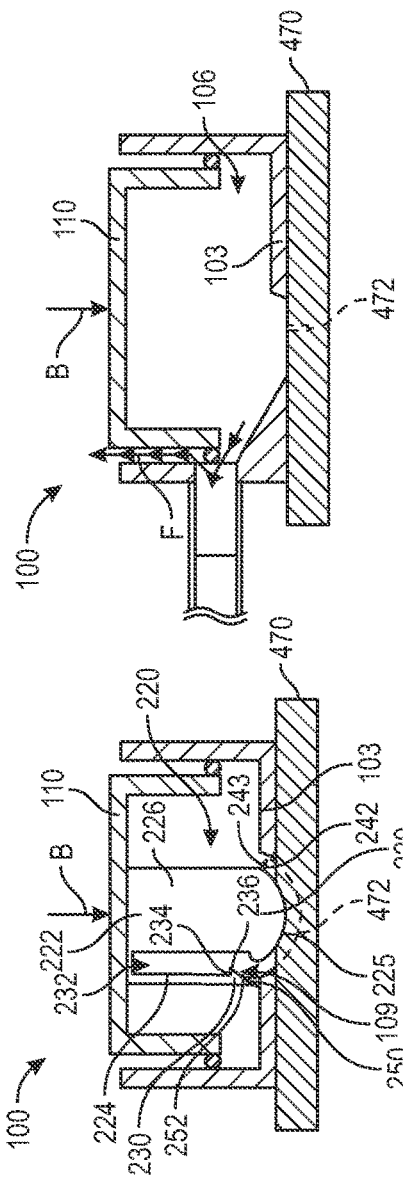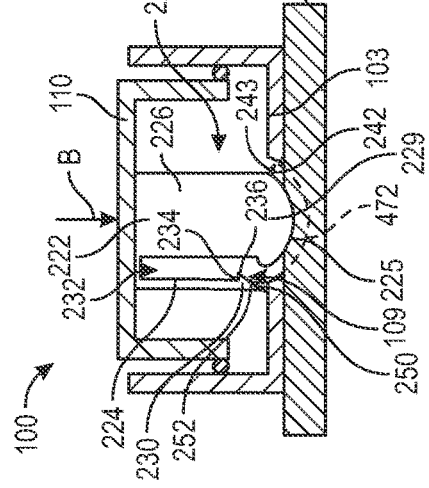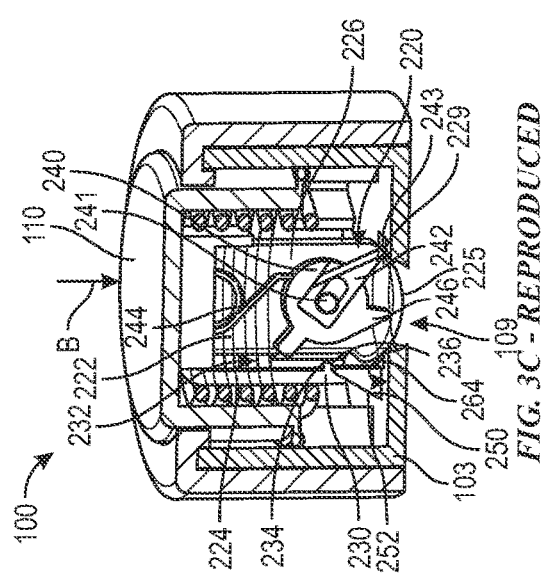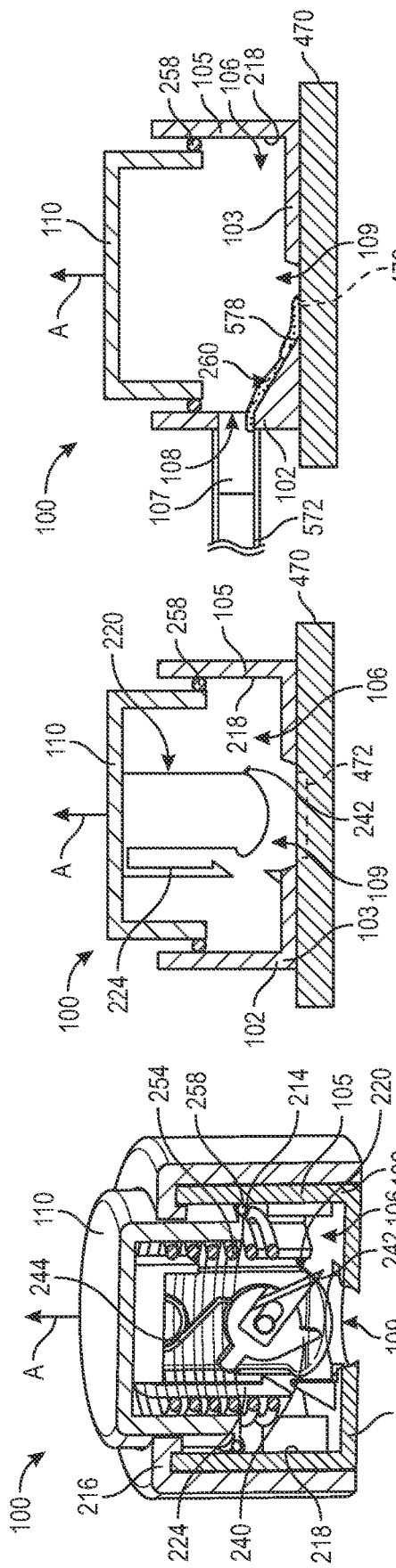

BODILY FLUID COLLECTION DEVICES AND RELATED METHODS

CROSS-REFERENCE TO RELATED APPLICATION

This application claims the benefit of U.S. Provisional Patent Application No. 63/154,537, filed Feb. 26, 2021, and titled "BODILY FLUID COLLECTION DEVICES AND RELATED METHODS," which is incorporated herein by reference in its entirety.

TECHNICAL FIELD

The present technology is related to collecting bodily fluid from a subject and, in particular, to handheld bodily fluid collection devices and related methods.

BACKGROUND

Devices, systems, and methods to collect bodily fluids, such as blood, are widely used in personalized, clinical, and field medical applications. Biological samples are commonly collected using simple lancing devices or more sophisticated devices that require trained personnel (e.g., phlebotomy venipunctures). Transferring bodily fluids to a container, receptacle, or an analysis device often requires several steps, which can be time consuming, prone to error, and/or cumbersome. Moreover, many personalized devices designed for untrained users can obtain only very limited volumes of bodily fluid, which in turn limits the applicability of such devices.

BRIEF DESCRIPTION OF THE DRAWINGS

Many aspects of the present technology can be better understood with reference to the following drawings. The components in the drawings are not necessarily to scale. Instead, emphasis is placed on clearly illustrating the principles of the present technology.

FIG. 6 reproduces FIGS. 3A, 4A, and 5A and FIGS. 3B, 4B, and 5B in side-by-side form to illustrate the movement of the device between a pre-deployed position and a partially deployed position.

FIG. 7 reproduces FIGS. 3C, 4C, and 5C and FIGS. 3D, 4D, and 5D in side-by-side form to illustrate the movement of the device between a deployed position and a post-deployed position.

DETAILED DESCRIPTION

Figure 1A:
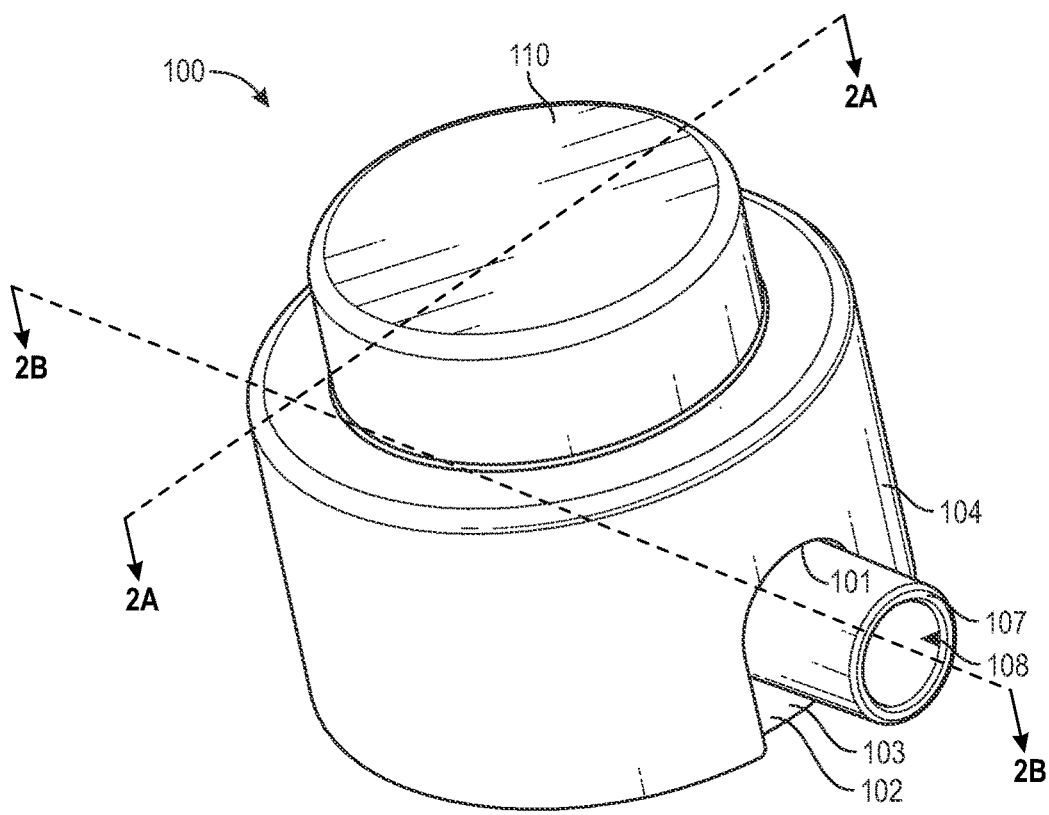
FIGS. 1A and 1B are top and bottom perspective views, respectively, of a bodily fluid collection device configured in accordance with embodiments of the present technology.

The present technology is directed generally to devices and methods for deploying a skin-piercing feature, such as a blade having a sharpened cutting edge, toward/into a subject's skin to withdraw and collect bodily fluid (e.g., blood). In some embodiments, a device for withdrawing bodily fluid from a subject can include a housing having a base configured to be positioned against the skin of the subject. The base can include an opening extending therethrough for collecting the bodily fluid. The device can further include an actuator movable relative to the housing and a skin-piercing assembly coupled to the actuator. The skin-piercing assembly can include (i) a casing, (ii) a drive member pivotably mounted within the casing and carrying a blade, and (iii) a biasing member (e.g., a torsion spring) coupling the drive member to the casing. In some embodiments, the actuator can be movable relative to the housing from a pre-deployed position to a deployed position. In the pre-deployed position, the drive member can engage the casing to maintain the biasing member in a biased configuration. Movement of the actuator from the pre-deployed position to the deployed position can disengage the drive member from the casing to permit the biasing member to drive the blade at least partially through and/or across the opening in the base to incise the skin of the subject.

More specifically, in some embodiments the casing can include a trigger portion spaced apart from a blade holder portion. The drive member can be pivotally mounted within the blade holder portion, and can include a first retaining feature (e.g., a tab or protrusion) that engages a second retaining feature (e.g., an adjacent tab or protrusion) on the trigger portion to lock the drive member in the pre-deployed position. The housing can further include a release member (e.g., a ramp) positioned on the base below the trigger portion. Movement of the actuator to the deployed position can engage the trigger portion with the release member to deflect the trigger portion away from the blade holder portion to disengage the first and second retaining features to allow the biasing member to rotate the drive member.

In some embodiments, the casing can have a shaped lower surface configured to extend at least partially through the opening in the base and to contact the skin in the deployed position. In some embodiments, the lower surface can depress the skin of the subject to form the skin to a predetermined shape. In some embodiments, the lower surface can have a gap between two flat portions configured to receive a portion of the skin of the subject. In some embodiments, the shape of the lower surface can generally match (e.g., be concentric with) an arcuate/sweeping path of the blade through the opening. Accordingly, the resulting incision can have a generally uniform depth and/or a rectangular shape. In other embodiments, the shape of the lower surface can be selected based on other desired shapes and/or dimensions of the resulting incision.

In some embodiments, the housing can include a sidewall and a connector extending from the sidewall. A collection reservoir (e.g., a tube) can be sealingly mounted to the connector for receiving bodily fluid. The housing and the actuator can at least partially define an enclosed region, and the device can further include a sealing member coupled to the actuator and configured to seal an interface between the actuator and the sidewall of the housing. The enclosed region can be sealed (e.g., sealed from an environment external to the device) when the device is placed against the skin of the subject the collection tube is mounted to the connector. In some embodiments, movement of the actuator in a deployment direction toward the base can decrease the volume of the enclosed region and advance the sealing member at least partially past or adjacent to the channel in the connector to permit a pressure in the enclosed region to equalize via a fluid path extending (i) from the enclosed region, (ii) through the channel past the sealing member, and (iii) between the actuator and the sidewall to outside the housing. The device can further include a retraction actuator configured to drive the actuator in a retraction direction (e.g., opposite the deployment direction) from the deployed position to a retracted position. In some embodiments, the retraction of the actuator can increase the volume of the enclosed region and advance the sealing member along the sidewall above the channel such that the pressure in the enclosed region is reduced. Accordingly, in some aspects of the present technology the device can be auto-venting upon deployment of the actuator (e.g., upon user depression of the actuator) and auto-vacuum generating upon retraction of the actuator (e.g., upon user release of the actuator).

Specific details of several embodiments of the present technology are described herein with reference to FIGS. 1A-13B. However, the present technology may be practiced without some of these specific details. In some instances, well-known structures and techniques often associated with bodily fluid collection devices have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

Figure 1B:
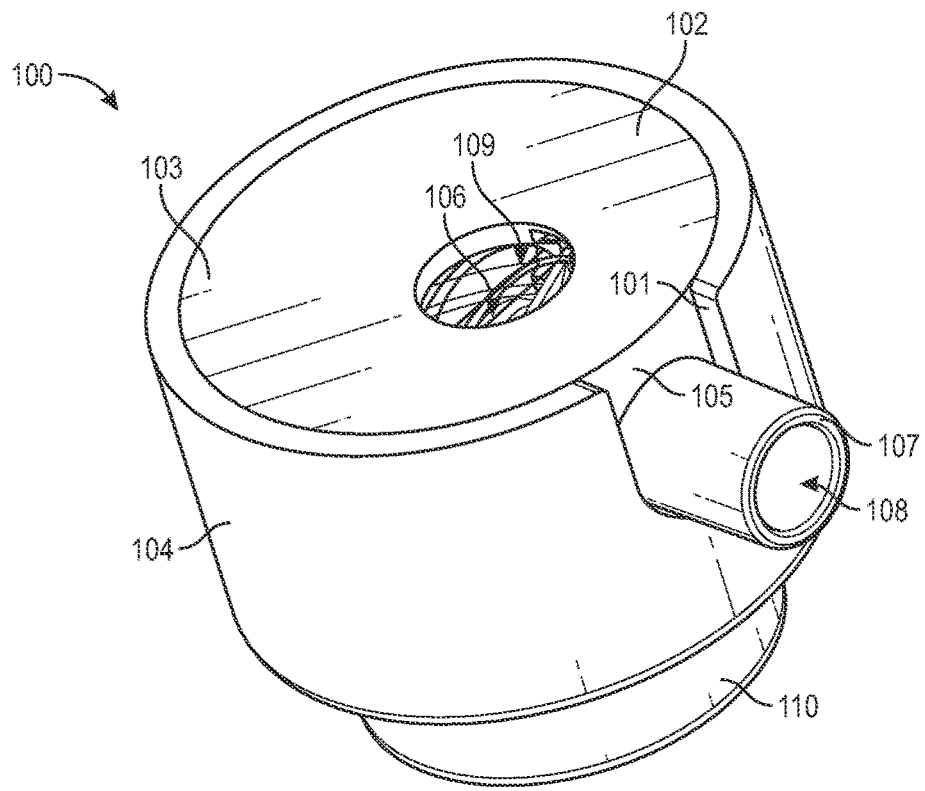

FIGS. 1A and 1B are top and bottom perspective views, respectively, of a bodily fluid collection device 100 ("device 100") configured in accordance with embodiments of the present technology. In some embodiments, the device 100 has some features generally similar or identical to, and/or operate generally similarly or identically to, any of the bodily fluid collection devices disclosed in U.S. patent application Ser. No. 17/006,246, titled "BODILY FLUID COLLECTION DEVICES AND RELATED METHODS," and filed Aug. 28, 2020, which is incorporated herein by reference in its entirety. For example, the device 100 can be handheld with a size that is easily grasped and manipulated by one or both of a subject's hands. Such handheld devices advantageously allow a subject to collect a bodily fluid sample (e.g., a blood sample) without assistance from another individual. In some embodiments, the bodily fluid collection devices of the present technology can be operated by a layperson outside of a medical setting (e.g., at home or in a field clinic) and without the aid of a medical professional.

Referring to FIGS. 1A and 1B together, in the illustrated embodiment the device 100 includes a first (e.g., lower) housing 102 and a second (e.g., upper) housing 104 that can be secured together via, for example, an interference fit, adhesives, fasteners, and so on. In other embodiments, the first and second housings 102, 104 can be integrally formed together. The first and second housings 102, 104 can have the illustrated circular cross-sectional shape while, in other embodiments, the first and second housings 102, 104 can have other cross-sectional shapes such as rectangular, square, rectilinear, polygonal, irregular, and so on. In some embodiments, the second housing 104 can be positioned around the first housing 102 (e.g., such that the first housing 102 is nested in the second housing 104).

In the illustrated embodiment, the device 100 further includes an actuator 110 movably coupled to and/or within the first housing 102 and/or the second housing 104. The actuator 110, the first housing 102, and/or the second housing 104 can together define an enclosed region 106 (e.g., an enclosed space, an enclosed volume, a lumen, a chamber). In some embodiments, the actuator 110 is movable to increase/decrease a volume of the enclosed region 106. The first housing 102 can include a base 103, a sidewall 105 extending from the base 103, and a connector 107 extending from the sidewall 105. In some embodiments, the sidewall 105 extends generally perpendicular to the base 103 and/or the connector 107 extends generally perpendicular to the sidewall 105. The base 103 includes/defines an opening 109 extending therethrough and opening to the enclosed region 106. In the illustrated embodiment, the opening 109 is circular while, in other embodiments, the opening 109 can have other shapes such as rectangular, square, rectilinear, polygonal, irregular, and so on. The connector 107 can define a channel 108 in fluid communication with the enclosed region 106, and is configured to be removably coupled to a collection reservoir (not shown; e.g., a collection tube/cartridge/reservoir 572 shown in FIGS. 5A-5D) for receiving bodily fluid withdrawn from a subject. In some embodiments, the collection reservoir can act as a removable and standardized container for bodily fluid that can be detached and inserted into clinical and laboratory equipment or workflows (e.g., for diagnostics and/or biomarker detection). In some embodiments, the second housing 104 can include a cut-out region 101 configured to be positioned about/over the connector 107.

In general, to collect a bodily fluid sample, the device 100 is applied to a subject's body (not shown) with the base 103 positioned against the skin of the subject and the actuator 110 positioned away from the skin (similar to the configuration illustrated in FIG. 1A). Actuating (e.g., pressing, twisting, pulling) the actuator 110 can deploy a skin-piercing feature (e.g., a blade, lancet) through the opening 109 from within the device 100 to pierce the subject's skin. In some embodiments, the device 100 is configured to generate a vacuum within the device 100 that acts against the subject's skin, either directly or indirectly and before and/or after deployment of the skin-piercing feature. For example, movement of the actuator 110 away from the base 103 can increase the volume of the enclosed region 106 to generate vacuum pressure therein. Bodily fluid from the resulting incision is withdrawn into the enclosed region 106 and collected into a collection reservoir (not shown) removably coupled to the connector 107.

Figure 2A:
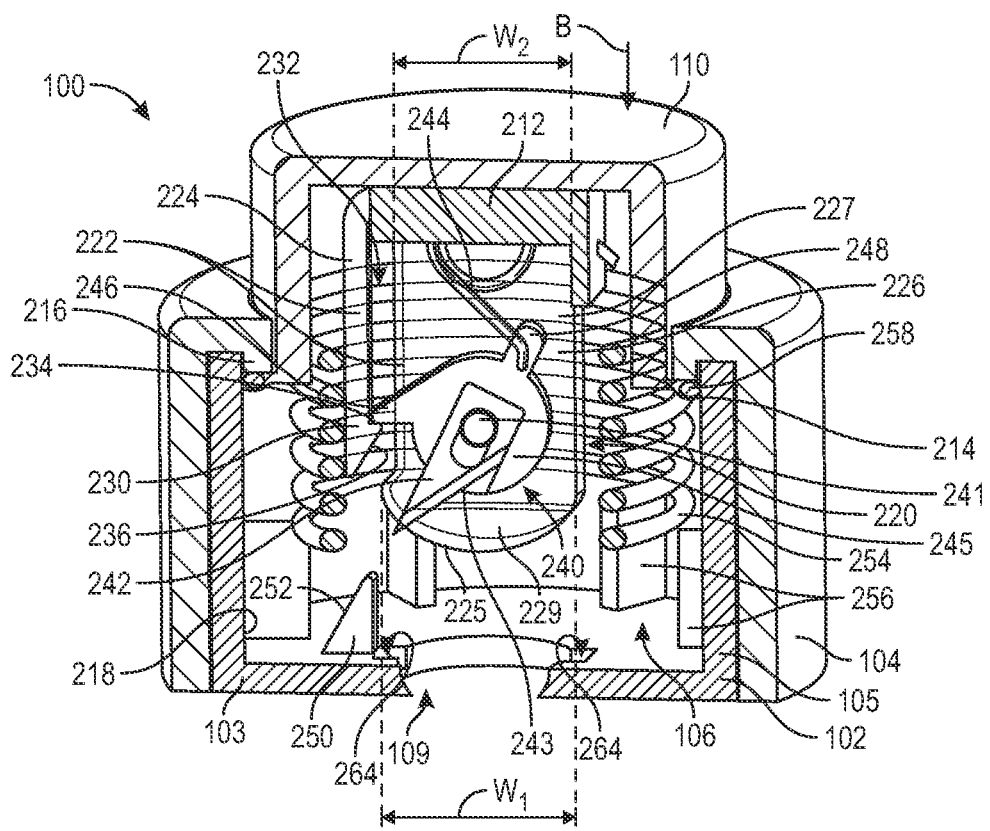
FIGS. 2A and 2B are side-cross sectional views of the device of FIGS. 1A and 1B taken along the lines 2A-2A and 2B-2B in FIG. 1A, respectively, in accordance with embodiments of the present technology.
Figure 2B:
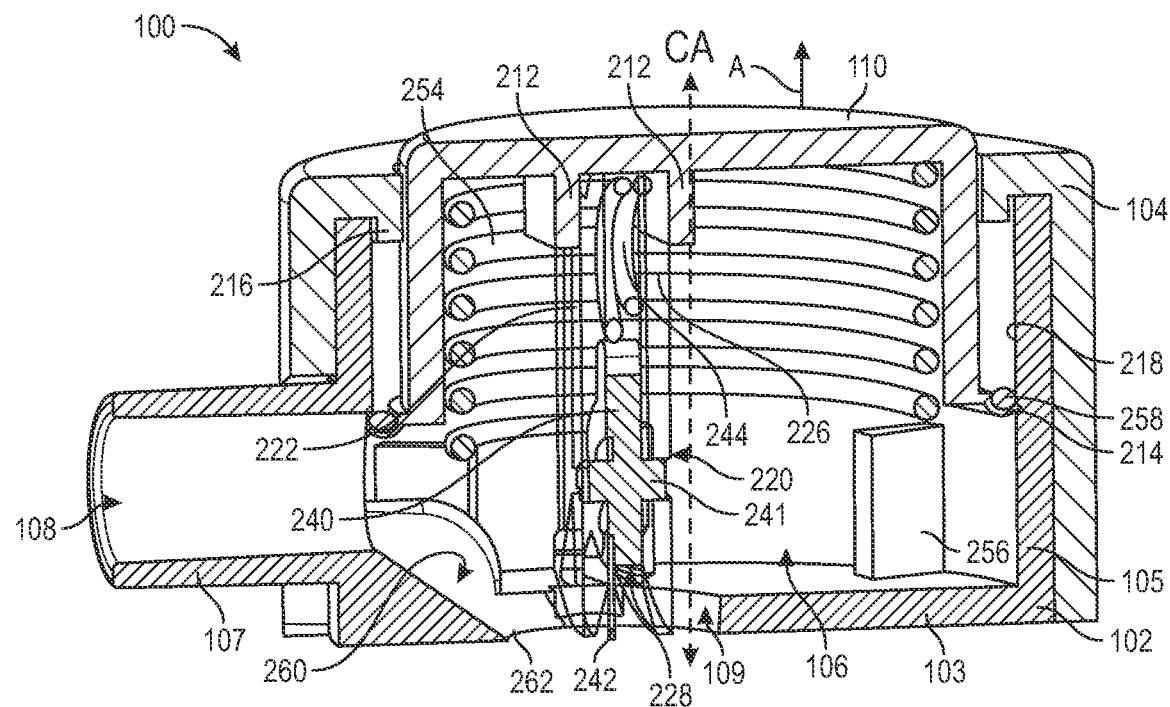
Figure 2C:
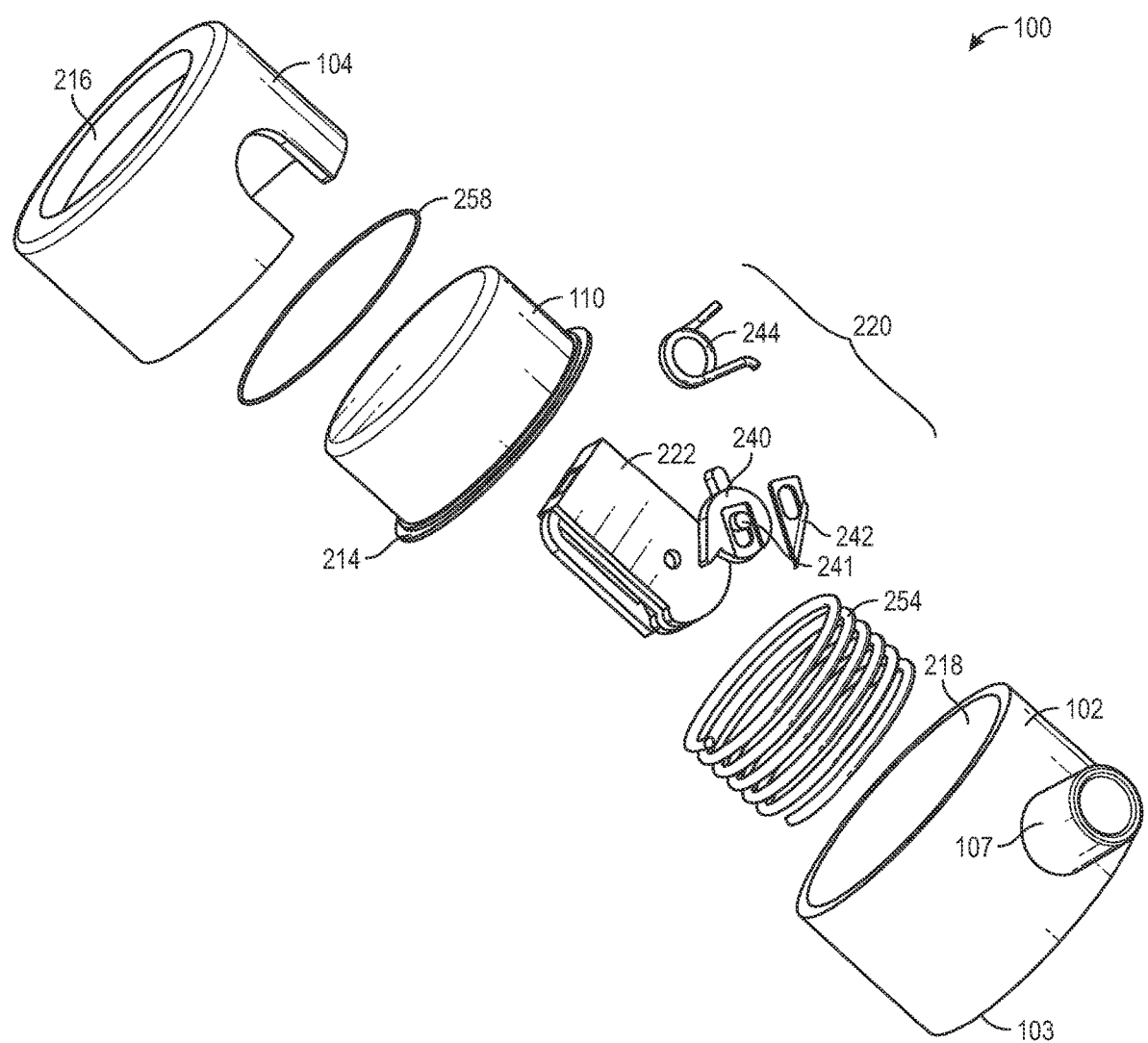
FIG. 2C is an exploded view of the device of FIGS. 1A and 1B in accordance with embodiments of the present technology.

FIGS. 2A and 2B are side-cross sectional views of the device 100 taken along the lines 2A-2A and 2B-2B in FIG. 1A, respectively, and FIG. 2C is an exploded view of the device 100 configured in accordance with embodiments of the present technology. Referring to FIGS. 2A-2C together, the device 100 includes a skin-piercing assembly 220 coupled to the actuator 110 and at least partially positioned within the enclosed region 106. The device 100 is in a pre-deployed position in FIG. 2A, and the device 100 is in a partially deployed position in FIG. 2B. As described in detail below with reference to FIGS. 3A-5D, the device 100 is further movable to a deployed position and a retracted position.

Referring first to FIG. 2A, in the illustrated embodiment the skin-piercing assembly 220 includes a casing 222 (e.g., a cartridge, a housing, an enclosure) having a trigger portion 224 and a blade holder portion 226. The casing 222 is shown as partially transparent in FIGS. 2A and 2B for clarity. In the illustrated embodiment, the blade holder portion 226 defines a channel 228 (FIG. 2B) and includes an upper region 227 having a generally rectangular shape and a lower region 229 having a curved or bulbous shape defined at least in part by a curved lower edge/surface 225. In the illustrated embodiment, the trigger portion 224 has a generally elongate shape and includes a first retaining feature 230. The trigger portion 224 can be spaced apart from at least a portion of the blade holder portion 226 to define a channel 232. The first retaining feature 230 can project at least partially into the channel 232 in a direction toward the blade holder portion 226 and can include a retaining surface 234 and a first actuation surface 236.

The trigger portion 224 and/or the blade holder portion 226 can be coupled to the actuator 110 (e.g., a lower surface thereof) such that movement of the actuator 110 moves the skin-piercing assembly 220 through the enclosed region 106. For example, the upper region 227 of the blade holder portion 226 can be secured within a corresponding recessed portion 212 of the actuator 110 via an interference fit, adhesive, and/or fasteners. In other embodiments, the actuator 110 and the casing 222 can be integrally formed together.

The skin-piercing assembly 220 can be coupled to the actuator 110 over the opening 109 in the base 103. As best seen in FIG. 2B, in the illustrated embodiment the opening 109 and the skin-piercing assembly 220 are positioned nearer to the connector 107 than an opposing portion of the sidewall 105. That is, the opening 109 and/or the skin-piercing assembly 220 can be laterally offset relative to a central axis CA (FIG. 2B) of the device 100. In other embodiments, the opening 109 and/or the skin-piercing assembly 220 can be positioned along the central axis CA or differently with respect to the central axis CA.

Referring again to FIGS. 2A-2C together, the skin-piercing assembly 220 further includes (i) a drive member 240 pivotably/rotatably mounted within the blade holder portion 226 of the casing 222, (ii) a skin-piercing feature, such as a blade 242, coupled to the drive member 240, and (iii) a first biasing member 244 operably coupling the drive member 240 to the casing 222, the actuator 110, and/or another component of the device 100. More specifically, with reference to FIGS. 2A and 2B, the drive member 240 can be positioned within the channel 228 (FIG. 2B) in the blade holder portion 226 and pivotably coupled to the blade holder portion 226 at a pivot axis 241 (e.g., a shaft, a rotation axis, an elongate member). In some embodiments, the lower region 229 of the blade holder portion 226 has a maximum width $W_1$ (FIG. 2A) that is greater than a width $W_2$ (FIG. 2A) of the upper region 227, and the blade 242 can extend farther from the pivot axis 241 than the second retaining feature 246. In some aspects of the present technology, this can inhibit the second retaining feature 246 from extending past the lower surface 225 when the blade 242 is triggered to rotate as described in detail below.

Referring again to FIG. 2A, in the illustrated embodiment the blade 242 has a sharpened cutting edge 243 and is secured to/over the pivot axis 241. In other embodiments, other types of skin-piercing features can be used instead of or in addition to the blade 242 including, for example, one or more needles, lancets (e.g., cylindrical or other shaped lancets), and/or other features configured to pierce the skin of a subject. The drive member 240 can include a generally circular body 245, a second retaining feature 246 projecting from the body 245, and a spring mount 248 projecting from the body 245. In some embodiments, the first biasing member 244 can be a torsion spring or other suitable biasing member that is connected between the spring mount 248 and the casing 222 and/or the actuator 110. In the pre-deployed and partially-deployed positions shown in FIGS. 2A and 2B, respectively, (i) the first biasing member 244 is biased (e.g., under load) to rotate the drive member 240 about the pivot axis 241 in a counterclockwise direction and (ii) the second retaining feature 246 projects into the channel 232 between the trigger portion 224 and the blade holder portion 226 and abuts the retaining surface 234 of the first retaining feature 230. Accordingly, the contact between the first and second retaining features 230, 246 inhibits the drive member 240 (and the blade 242) from pivoting about the pivot axis 241 and maintains the first biasing member 244 in a biased state.

With continued reference to FIG. 2A, the device 100 further includes a release member 250 coupled to the base 103 of the first housing 102 (e.g., an upper surface thereof) within the enclosed region 106. The release member 250 can be attached to or integrally formed with the first housing 102 and is positioned below (e.g., vertically below) the trigger portion 224 of the casing 222. In the illustrated embodiment, the release member 250 includes a second actuation surface 252. As described in detail below with reference to FIGS. 3A-4D, movement of the actuator 110 toward the base 103 can drive the first actuation surface 236 of the first retaining feature 230 into contact with the second actuation surface 252 of the release member 250. The first and second actuation surfaces 236, 252 can be configured (e.g., shaped, sized, positioned, angled) such that downward movement of the first actuation surface 236 against the second actuation surface 252 drives/flexes the first retaining feature 230 away from the second retaining feature 246 to permit the first biasing member 244 to drive the drive member 240 about the pivot axis 241 to drive the blade 242 along/past the curved lower surface 225.

Referring again to FIGS. 2A-2C together, the device 100 can further include a second biasing member 254 operably coupled between the actuator 110 and the first housing 102. In some embodiments, the second biasing member 254 can be coupled to one or more mounts 256 extending from the base 103 or another part of the first housing 102, and can extend around (e.g., radially outside of) the skin-piercing assembly 220. In some embodiments, the second biasing member 254 is a compression spring, a coil spring, or the like configured to bias the actuator 110 away from the base 103 of the housing 102 in the direction indicated by arrow A in FIG. 2B. Accordingly, pressing the actuator 110 toward the base 103 in the direction indicated by arrow B in FIG. 2A (e.g., to move the device 100 from the pre-deployed position to the partially-deployed position) can increase the load on the second biasing member 254. In the illustrated embodiment, the actuator 110 includes a flange 214 configured to operably engage (e.g., abut) a stop portion 216 of the second housing 104 in the pre-actuated position (FIG. 2A). The engagement of the flange 214 with the stop portion 216 inhibits the second biasing member 254 from driving the actuator 110 farther in the direction of the arrow A from its position in the pre-deployed position (e.g., out of the second housing 104).

In the illustrated embodiment, the device 100 further includes a sealing member 258 positioned circumferentially about the actuator 110 and configured to seal an interface between the first housing 102 and the actuator 110. In some embodiments, the sealing member 258 can be an O-ring, gasket, or the like positioned on and/or coupled to the flange 214 of the actuator 110. The sealing member 258 can sealingly engage an inner surface 218 of the sidewall 105 of the first housing 102 as the actuator 110 moves along the sidewall 105 in the direction of either of the arrows A and B.

As best seen in FIG. 2B, the base 103 of the first housing 102 can define/include a fluidic channel 260 extending from the opening 109 in the base 103 to the channel 108 in the connector 107. In some embodiments, the fluidic channel 260 can be configured (e.g., shaped, sized, angled, positioned, coated) to promote the flow of bodily fluid (e.g., blood) from the opening 109 and into the channel 108 and/or a collection reservoir fluidly connected thereto. In some embodiments, the fluidic channel 260 can be configured in accordance with any of the fluidic channels described in detail in (i) U.S. patent application Ser. No. 13/949,108, filed Jul. 23, 2013, and titled "METHODS, SYSTEMS, AND DEVICES RELATING TO OPEN MICROFLUIDIC CHANNELS", and/or (ii) U.S. patent application Ser. No. 14/816,994, filed Aug. 3, 2015, and titled "DEVICES, SYSTEMS AND METHODS FOR GRAVITY-ENHANCED MICROFLUIDIC COLLECTION, HANDLING AND TRANSFERRING OF FLUIDS", both of which are incorporated herein by reference in their entireties.

In the illustrated embodiment, the base 103 further includes a narrowed (e.g., razor) edge 262 adjacent to the fluidic channel 260 and at least partially defining the opening 109. In some aspects of the present technology, the shape (e.g., narrowness) of the edge 262 can inhibit bodily fluid from pooling proximate the interface between the opening 109 and the fluidic channel 260 and/or promote flowing of the bodily fluid from the opening 109 into the fluidic channel 260. Referring to FIG. 2A, in some embodiments the base 103 can further include cut-outs 264 (e.g., recesses, openings, channels) positioned adjacent the opening 109 and configured (e.g., shaped, sized, angled) to receive at least a portion of the skin-piercing assembly 120 therein in the partially-deployed position and/or the deployed position (e.g., as shown in FIGS. 3C and 4C).

Referring again to FIGS. 2A-2C together, the various components of the device 100 can comprise metal, plastic, and/or other suitable materials. For example, in some embodiments the first housing 102, the second housing 104, the actuator 110, the casing 222 of the skin-piercing assembly 220, the drive member 240, and/or other components of the device 100 can be 3D-printed, molded (e.g., injection molded), or otherwise formed from a plastic material. In some embodiments, some of the components can be snapped together or otherwise secured together after being individually manufactured. For example, the casing 222 of the skin-piercing assembly 220 can be manufactured in two parts before being joined together with the drive member 240, blade 242, and first biasing member 244 positioned in the channel 228 therebetween. Similarly, in some embodiments the assembled skin-piercing assembly 220 can first be inserted into the recessed portion 212 of the actuator 110, then the actuator 110 can be inserted into the first housing 102 with the second biasing member 254 positioned therebetween, then the second housing 104 can be positioned over/around the first housing 102 to secure the actuator 110 in position, and so on.

Operation of the device 100 to withdraw bodily fluid (e.g., blood) from a subject is illustrated in FIGS. 3A-5D. More specifically, FIGS. 3A-3D are side cross-sectional views of the device 100 taken along the line 2A-2A in FIG. 1A in accordance with embodiments of the technology; FIGS. 4A-4D are simplified side cross-sectional views of the device 100 taken along the line 2A-2A in FIG. 1A and placed against skin 470 of a subject in accordance with embodiments of the present technology; and FIGS. 5A-5D are simplified side cross-sectional views of the device 100 taken along the line 2B-2B in FIG. 1A and placed against the skin 470 of the subject in accordance with embodiments of the present technology. The casing 222 of the skin-piercing assembly 220 is shown as partially transparent in FIGS. 3A-3D for clarity. Certain components of the device 100 are omitted in FIGS. 4A-5D to more clearly illustrate the functioning of the skin-piercing assembly 220 and the sealing member 258, respectively. For example, the second housing 104 and the second biasing member 254 are omitted in FIGS. 4A-4D; and the second housing 104, the second biasing member 254, and the skin-piercing assembly 220 are omitted in FIGS. 5A-5D.

Figure 3A:
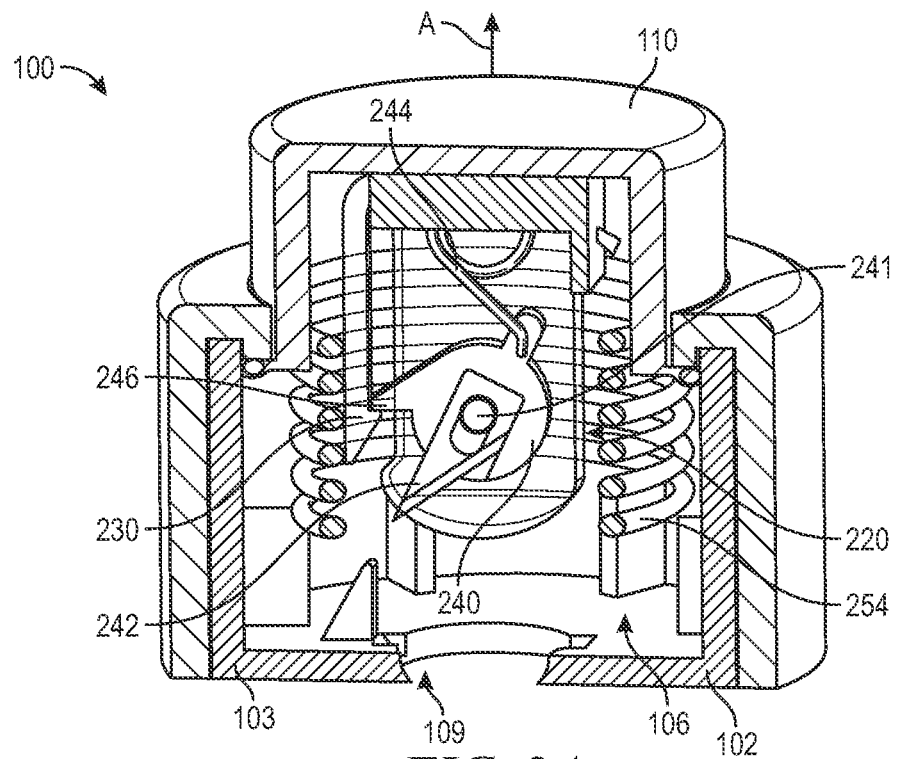
FIGS. 3A-3D are side cross-sectional views of the device taken along the line 2A-2A in FIG. 1A and at different stages of a method of withdrawing bodily fluid from a subject in accordance with embodiments of the technology.
Figure 3B:
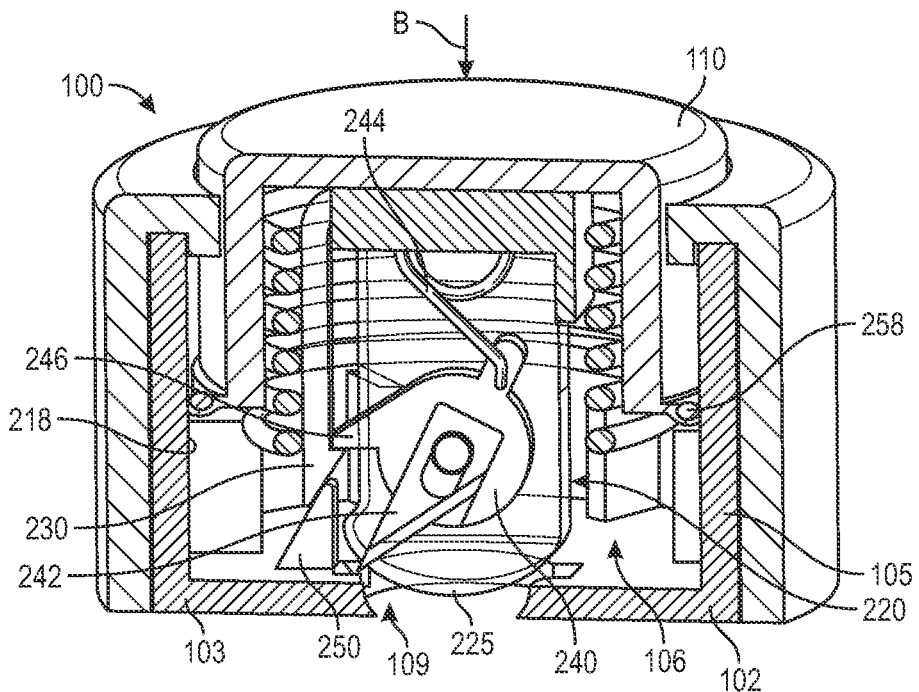
Figure 3C:
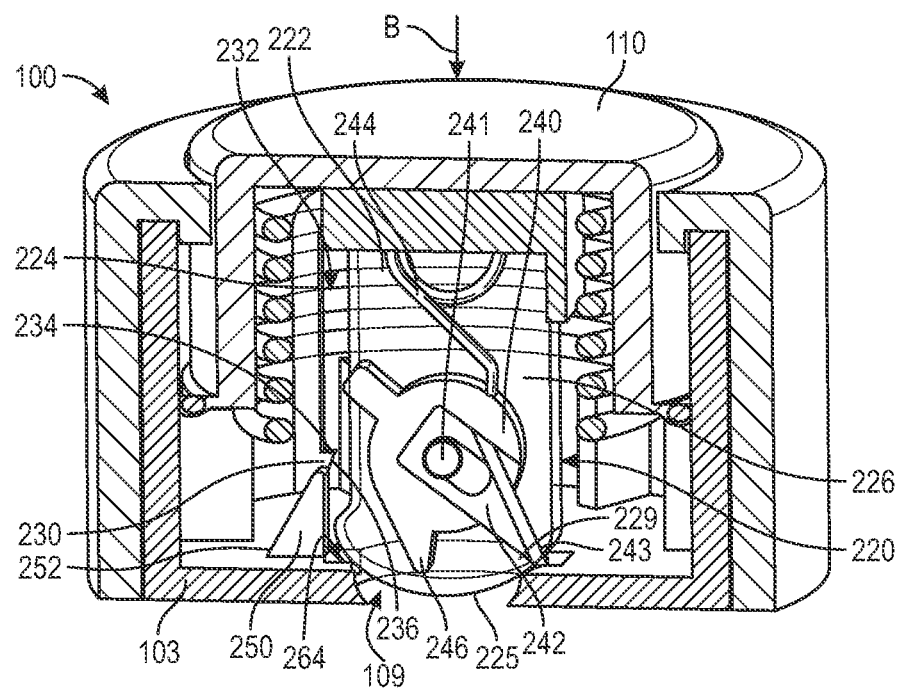
Figure 3D:
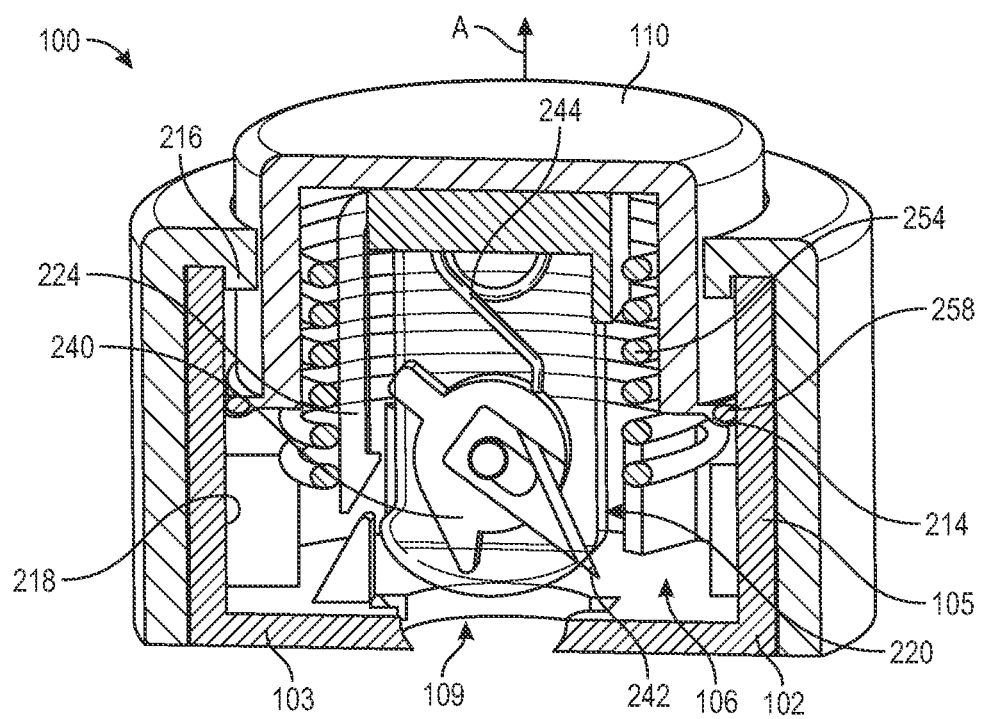
Figure 4A:
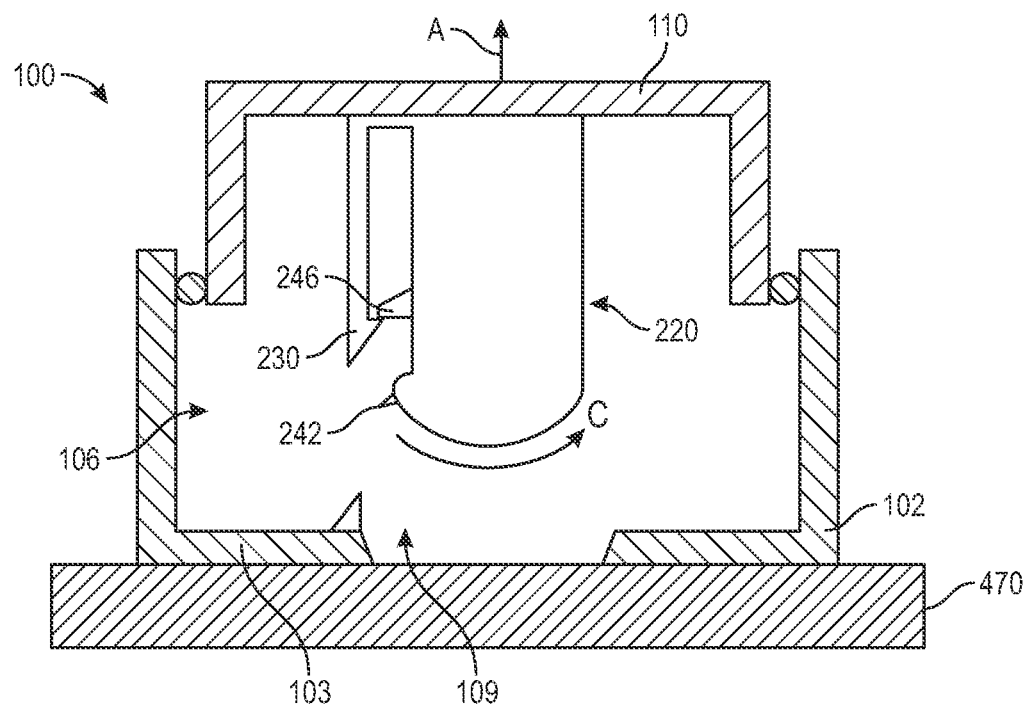
FIGS. 4A-4D are simplified side cross-sectional views of the device taken along the line 2A-2A in FIG. 1A and placed against skin of a subject at different stages of the method of withdrawing bodily fluid from the subject in accordance with embodiments of the present technology.
Figure 4B:
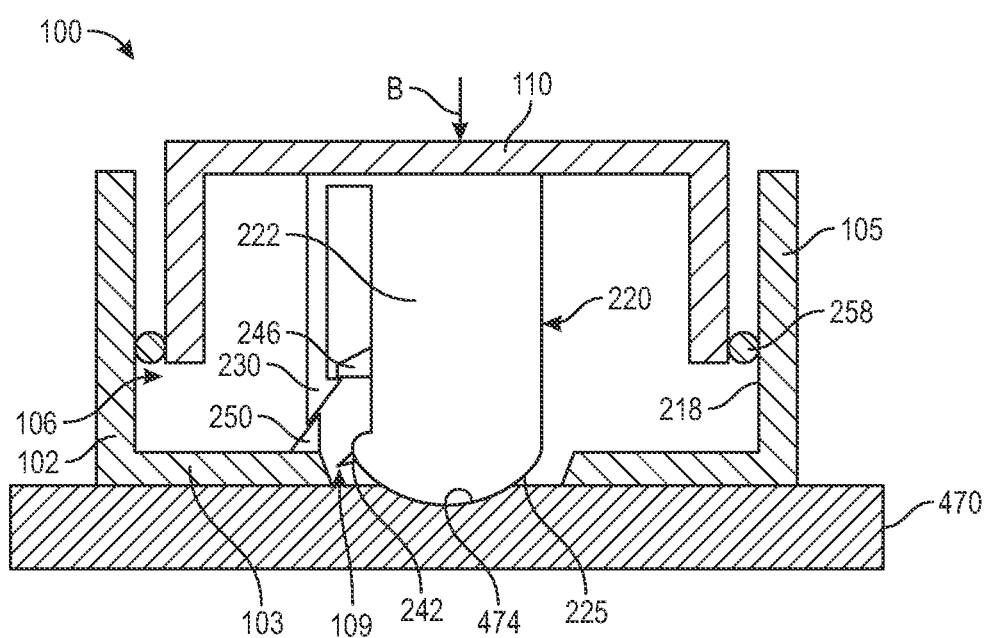
Figures 4C, 4D:
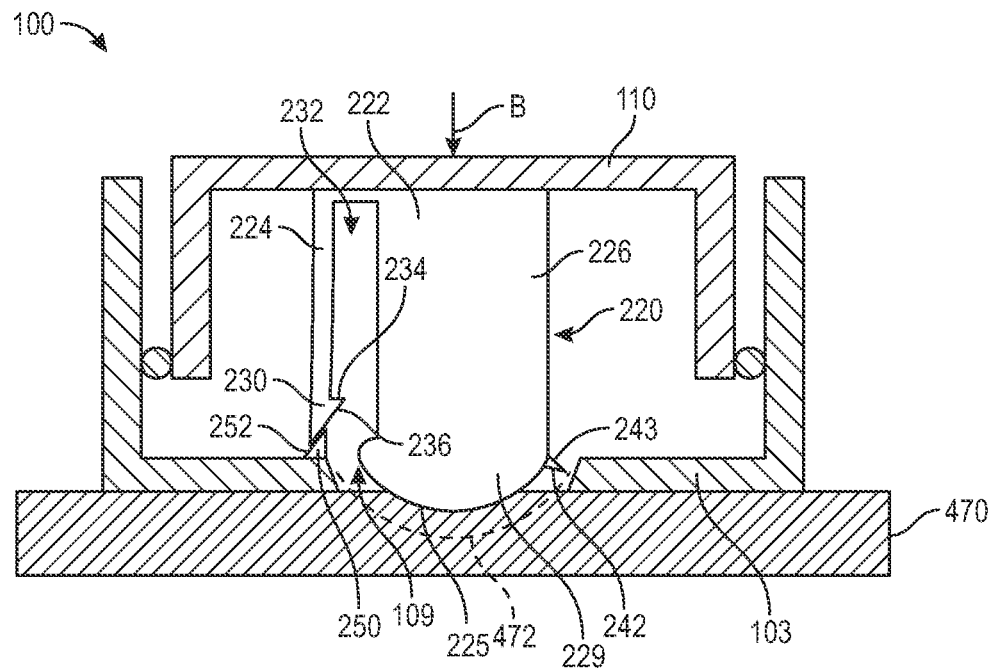
Figure 5A:
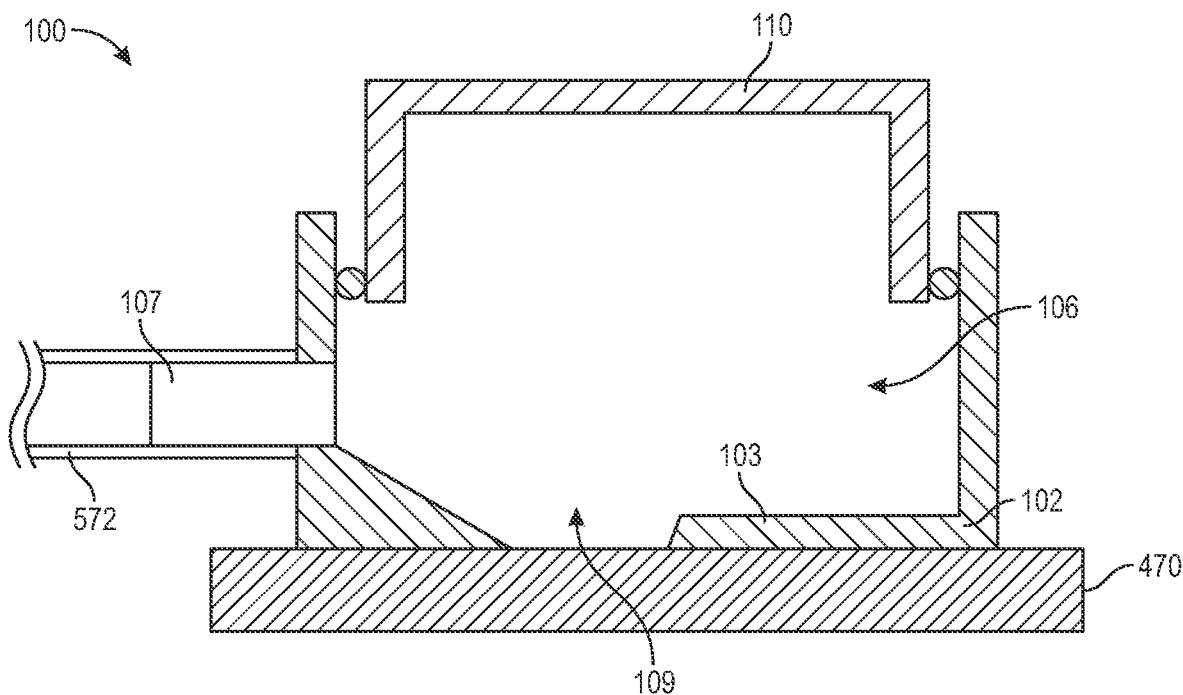
FIGS. 5A-5D are simplified side cross-sectional views of the device taken along the line 2B-2B in FIG. 1A and placed against the skin of the subject at different stages of the method of withdrawing bodily fluid from the subject in accordance with embodiments of the present technology.

In FIGS. 3A, 4A, and 5A, the device 100 is in the pre-deployed position (which can also be referred to as a first position, a ready position, a pre-actuated position, and the like). The device 100 is in the partially-deployed position in FIGS. 3B, 4B, and 5B (which can also be referred to as a second position, a skin-forming position, and the like). FIGS. 3C, 4C, and 5C illustrate the device 100 in the deployed position (which can also be referred to as a third position, a cutting position, a skin-piercing position, an actuated position, and the like). The device 100 is in the post-deployed position in FIGS. 3D, 4D, and 5D (which can also be referred to as a retracted position, a vacuum generation position, a post-actuated position, a fluid collection position and the like). FIGS. 3A, 4A, and 5A and FIGS. 3B, 4B, and 5B are reproduced side-by-side in FIG. 6 to further illustrate the movement of the device 100 between the pre-deployed and partially-deployed positions. FIGS. 3C, 4C, and 5C and FIGS. 3D, 4D, and 5D are reproduced side-by-side in FIG. 7 to further illustrate the movement of the device 100 between the deployed and post-deployed positions.

Referring first to FIGS. 3A, 4A, and 5A together, the device 100 can initially be placed against the skin 470 of the subject in the pre-deployed position. More specifically, the base 103 of the first housing 102 can be positioned against the skin 470 such that the opening 109 is over a portion of the skin 470. In some embodiments, the base 103 (e.g., a lower surface thereof) can sealingly engage the skin 470 around the opening 109. A collection reservoir 572 (FIG. 5A) can be secured to/over the connector 107 before or after the device 100 is applied against the skin 470 and can sealingly engage the connector 107 (FIG. 5A). Accordingly, the enclosed region 106 can be sealed after the device 100 is applied against the skin with the collection reservoir 572 secured to the connector 107. In some embodiments, the base 103 (e.g., a lower surface thereof) can include one or more features configured to increase the ability of the device 100 to seal against the skin of the subject. In some embodiments, for example, the base 103 can include a flexible membrane (not shown; e.g., a membrane 684 shown in FIGS. 6A and 6B) attached thereto.

Referring to FIGS. 3A and 4A together, and as described in detail above with reference to FIG. 2A, in the pre-deployed position the second biasing member 254 (FIG. 3A) biases the actuator 110—and the skin-piercing assembly 220 attached thereto—away from the opening 109 in the base 103 in the direction indicated by the arrow A (e.g., a retraction direction). Additionally, the first biasing member 244 biases the drive member 240 to rotate in the counterclockwise direction indicated by arrow C in FIG. 4A. However, the engagement of the first and second retaining features 230, 246 inhibits the drive member 240 (and the blade 242) from pivoting about the pivot axis 241. Accordingly, the skin-piercing assembly 220 is in a loaded or ready-to-fire state.

Figure 5B:
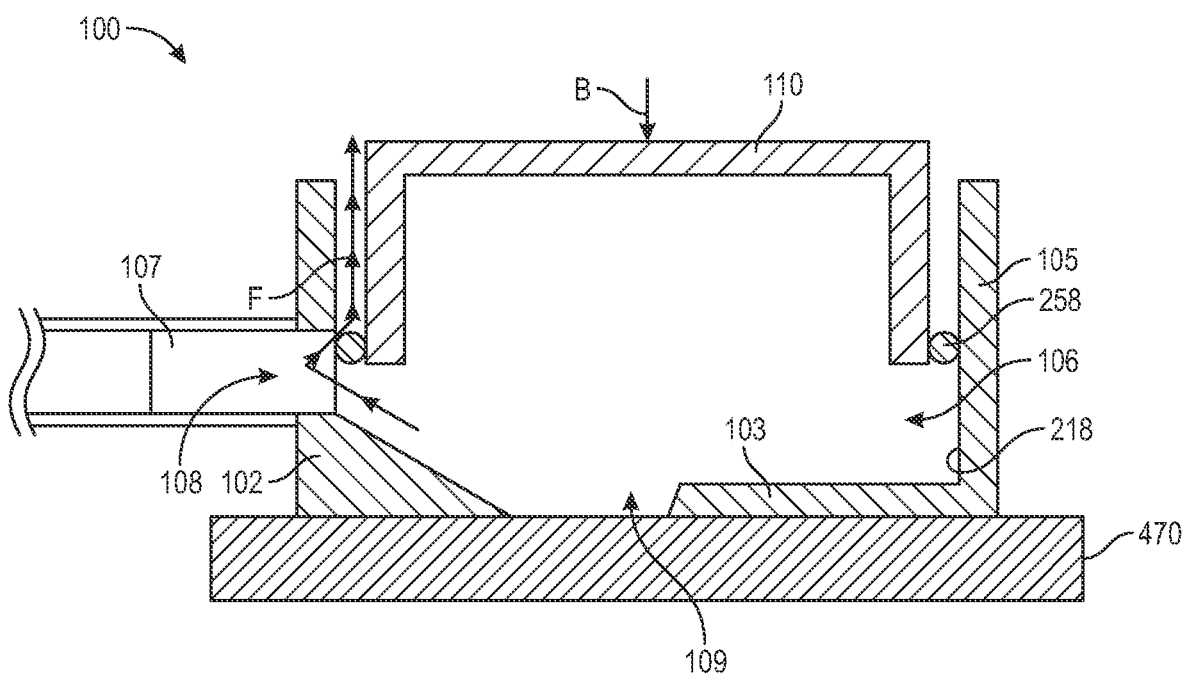
Figure 5C:
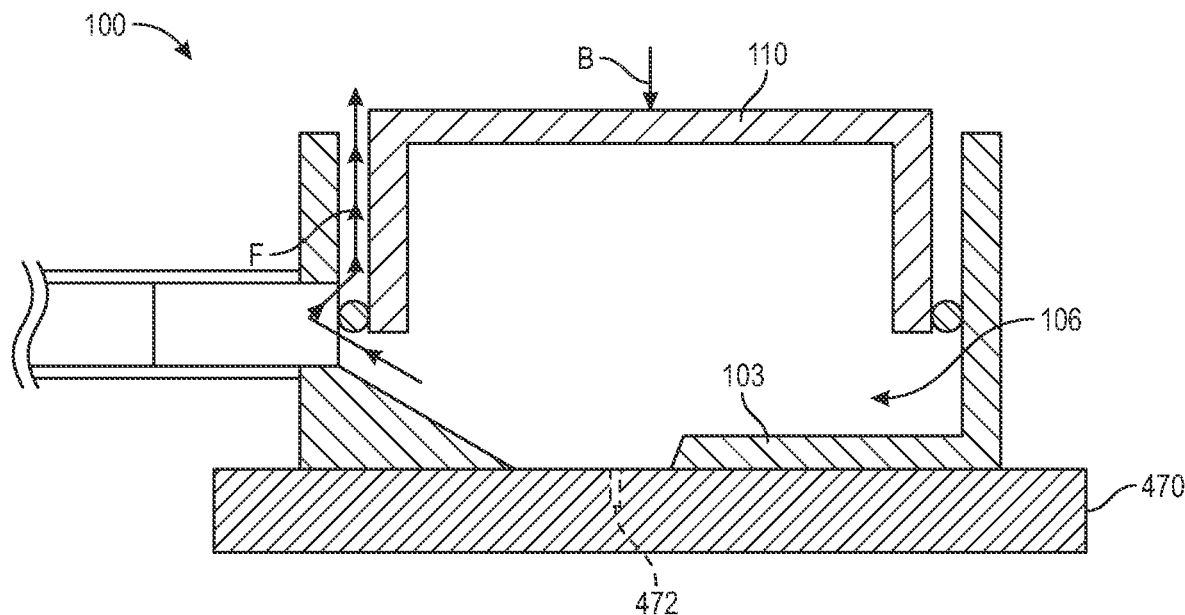

Referring next to FIGS. 3B, 4B, and 5B together, the device 100 can be moved from the pre-deployed position to the partially deployed position by moving (e.g., pressing by the subject or another) the actuator 110 toward the base 103 in the direction indicated by the arrow B (e.g., a deployment direction). With reference to FIGS. 3B and 4B together, moving the actuator 110 moves the skin-piercing assembly 220 through the enclosed region 106 and at least partially through the opening 109 in the base 103. More specifically, in some embodiments the curved lower surface 225 of the casing 222 can extend at least partially through the opening 109 to contact the skin 470 of the subject. In some embodiments, as shown in FIG. 4B, the casing 222 can depress the skin 470 of the subject to form a curved indentation 474 in the skin 470 that conforms to the shape of the lower surface 225. In other embodiments, the lower surface 225 can have other shapes (e.g., including undulations, flat portions, and so on), and the skin 470 can conform to the selected shape. Moreover, in the partially-deployed position, the first retaining feature 230 can be positioned above or slightly contact the release member 250 such that the first retaining feature 230 still inhibits the drive member 240 (and the blade 242) from releasing under the bias of the first biasing member 244. Moving the actuator 110 toward the base 103 also increases a load on (e.g., compresses) the second biasing member 254.

Referring again to FIGS. 3B, 4B, and 5B together, movement of the actuator 110 in the direction indicated by the arrow B initially drives the sealing member 258 along the inner surface 218 of the sidewall 105 of the first housing 102. Because the enclosed region 106 is sealed (e.g., via the sealed engagement of the base 103 with the skin 470, the collection reservoir 572 with the connector 107, and the sealing member 258 with the sidewall 105), the movement of the actuator 110 initially increases the pressure in the enclosed region 106 as the sealing member 258 moves along the sidewall 105 to decrease the volume of the enclosed region 106. However, referring to FIG. 5B, in the partially-deployed position the sealing member 258 can be positioned lower than (e.g., nearer to the base 103) than at least a portion of the channel 108 of the connector 107. That is, the sealing member 258 can move at least partially past and/or be positioned adjacent the channel 108. When the sealing member 258 passes the channel 108, the pressure in the enclosed region 106 is allowed to equalize as air is allowed to vent from the enclosed region 106, into the channel 108, and from the channel 108 between the actuator 110 and the inner surface 218 of the sidewall 105 to outside the device 100 (e.g., as indicated by fluid path F in FIG. 5B). Accordingly, in some aspects of the present technology the device 100 is configured to automatically vent air from the enclosed region 106 upon actuation of the actuator 110.

Referring next to FIGS. 3C, 4C, and 5C together, the device 100 can be moved from the partially-deployed position to the deployed position by continuing to move the actuator 110 toward the base 103 in the direction indicated by arrow B. With reference to FIGS. 3C and 4C together, continuing to move the actuator 110 moves the first retaining feature 230 of the trigger portion 224 into engagement with the release member 250 such that the first retaining feature 230 flexes away from and out of engagement with the second retaining feature 246. More specifically, the first actuation surface 236 and the second actuation surface 252 can be configured (e.g., shaped, angled, sized, positioned) to deflect the trigger portion 224 laterally to increase a width of the channel 232 (e.g., a width adjacent the first retaining feature 230). For example, in the illustrated embodiment the first and second actuation surfaces 236, 252 are formed as offset ramps. The trigger portion 224 can flex enough to release/disengage the second retaining feature 246 from the first retaining feature 230—such that the second retaining feature 246 no longer rests on the retaining surface 234.

When the second retaining feature 246 disengages the first retaining feature 230, the first biasing member 244 is configured to move from a biased stated to an at least partially relaxed state to thereby drive the drive member 240 to pivot about the pivot axis 241. As the drive member 240 pivots, the drive member 240 simultaneously moves (e.g., sweeps) the blade 242 along an arcuate path through and across at least a portion of the opening 109 (with the sharpened cutting edge 243 leading) to form an incision 472 in the skin 470 of the subject. In the illustrated embodiment, the blade 242 and the blade holder portion 226 of the casing 222 are configured (e.g., shaped, sized, and positioned) such that the blade 242 extends a generally uniform distance past the lower surface 225 of the casing 222 at each point along its path across the opening 109. That is, for example, the shape of the lower surface 225 can generally match (e.g., be concentric with) the arcuate path of the blade 242 (e.g., a tip of the blade). Accordingly, the resulting incision 472 can have a generally uniform depth. Moreover, as best seen in FIG. 4D, the incision 472 can have a generally rectangular shape. As described above, in other embodiments the lower surface 225 can have other shapes such that the skin 470 conforms to the specified shape of the lower surface 225. In such embodiments, the depth of the incision 472 will vary based on the selected shape of the lower surface 225. Accordingly, the shape and size of the lower surface 225 can be selected based on a desired shape and depth of the resulting incision.

In some embodiments, the casing 222 can contact the base 103 in the deployed position to precisely control the position of the blade 242 when its released. For example, the casing 222 can be configured (e.g., shaped, sized, positioned) to enter and/or contact the base 103 in the cut-outs 264. In some aspects of the present technology, this can ensure that the blade 242 moves through its arcuate path across/through the opening 109 at a predetermined position to, for example, allow for precise control of the depth and/or shape of the resulting incision 472.

In some embodiments, the first biasing member 244 is configured to reach a relaxed state after moving the blade 242 to the position shown in FIGS. 3C and 4C. In such embodiments, the first biasing member 244 can inhibit the blade 242 from rotating in either a clockwise or counter-clockwise direction after reaching the deployed position. In some embodiments, the blade 242 can abut a portion of the casing 222 and/or another portion of the device 100 in the deployed position to inhibit the first biasing member 244 from continuing to rotate the blade 242. That is, for example, the casing 222 can provide a stop for the blade 242.

In some embodiments, the blade 242 extends farther from the pivot axis 241 than the second retaining feature 246 such that the second retaining feature 246 does not extend past the lower surface 225 when the drive member 240 rotates to the deployed position. More particularly, the shape and size of the lower region 229 (e.g., the larger width $W_2$ shown in FIG. 2A) can block the second retaining feature 246 from extending past the lower surface 225 upon rotation of the blade 242. In some aspects of the present technology, this configuration can inhibit the second retaining feature 246 or any other portion of the drive member 240 from contacting the skin 470 of the user during deployment/firing of the blade 242.

Referring to FIG. 5C, in the deployed position, the enclosed region 106 remains open to the atmosphere around the device 100 via the fluid path F. Accordingly, the continued movement of the actuator 110 from the partially-deployed position to the deployed position does not change the pressure within the enclosed region 106—which remains at an equal pressure to the environment around the device 100.

Referring next to FIGS. 3D and 4D together, the device 100 can be moved from the deployed position to the post-deployed position by releasing the actuator 110 to allow the second biasing member 254 to drive the actuator 110 and the skin-piercing assembly 220 away from the base 103 in the direction indicated by the arrow A (e.g., in the retraction direction). The retraction of the actuator 110 can move the skin-piercing assembly 220 out of contact within the skin 470 and fully into the enclosed region 106. In some embodiments, with reference to FIGS. 2A and 3D together, the second biasing member 254 can return the actuator 110 to the pre-actuated position in which the flange 214 of the actuator 110 engages the stop portion 216 of the second housing 104. Nevertheless, the device 100 can be configured as a single-use device that cannot be redeployed. For example, in the illustrated embodiment the device 100 is configured such that subsequent actuation of the actuator 110 when the device 100 is in the post-deployed configuration does not pivot the blade 242 into the opening 109. Specifically, the first biasing member 244 is no longer biased in the post-deployed configuration (e.g., after the drive member 240 is released from the trigger portion 224) and therefore cannot drive the blade 242 through the opening 109. In other embodiments, the device 100 can have other features specifically configured to limit the device 100 to a single use. For example, the actuator 110 can be configured as a pass-through actuator that does not reengage the skin-piercing assembly 220 after use.

Figure 5D:
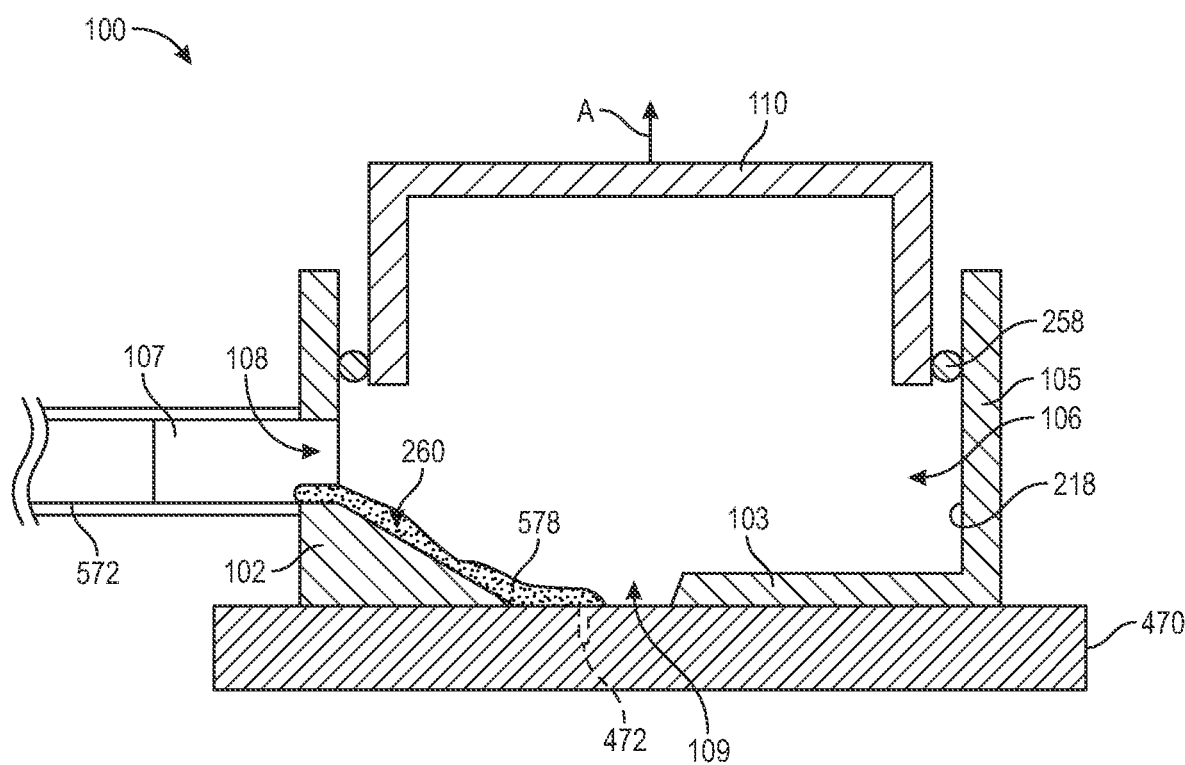

With reference to FIGS. 3D, 4D, and 5D together, retraction of the actuator 110 in the direction of the arrow B drives the sealing member 258 upward along the inner surface 218 of the sidewall 105 past the channel 108 of the connector 107 (FIG. 5D)—substantially eliminating the fluid path F shown in FIGS. 5B and 5C. That is, the sealing member 258 again sealingly engages an entire circumference of the inner surface 218 of the sidewall 105 such that the enclosed region 106 is sealed (e.g., via the sealed engagement of the base 103 with the skin 470, the collection reservoir 572 with the connector 107, and the sealing member 258 with the sidewall 105). Accordingly, the upward movement of the sealing member 258 along the sidewall 105 decreases the pressure in the enclosed region 106 to generate negative/vacuum pressure within the enclosed region 106. As shown in FIG. 5D, in some aspects of the present technology the vacuum pressure can help draw a bodily fluid 578 (e.g., blood) at least partially (i) from the incision 472, (ii) through the opening 109 into the enclosed region 106, (iii) along the fluidic channel 260, (iv) into the channel 108, and/or (v) into the collection reservoir 572.

Figure 8A:
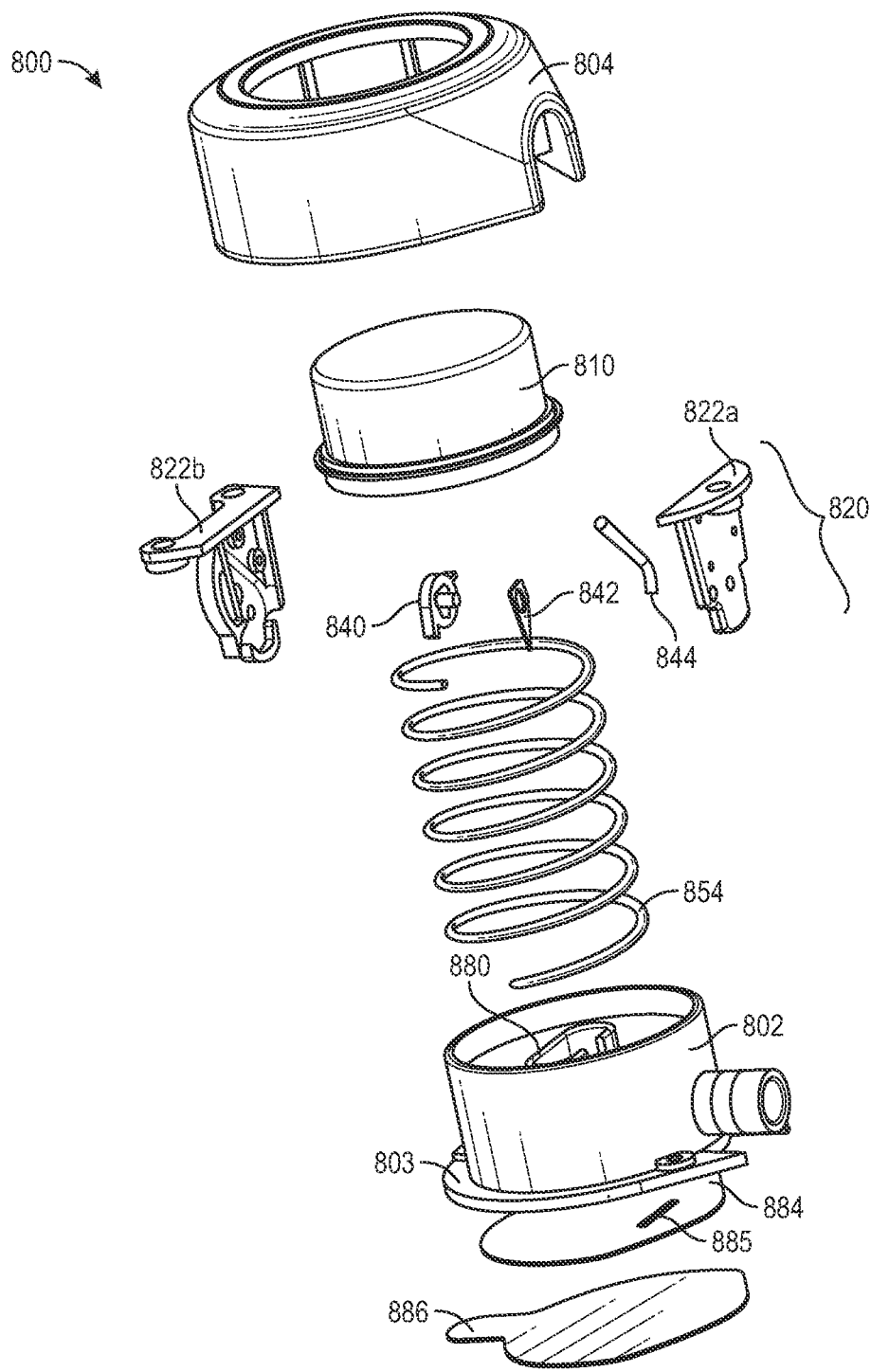
FIGS. 8A and 8B are exploded isometric views of a bodily fluid collection device configured in accordance with additional embodiments of the present technology.
Figure 8B:
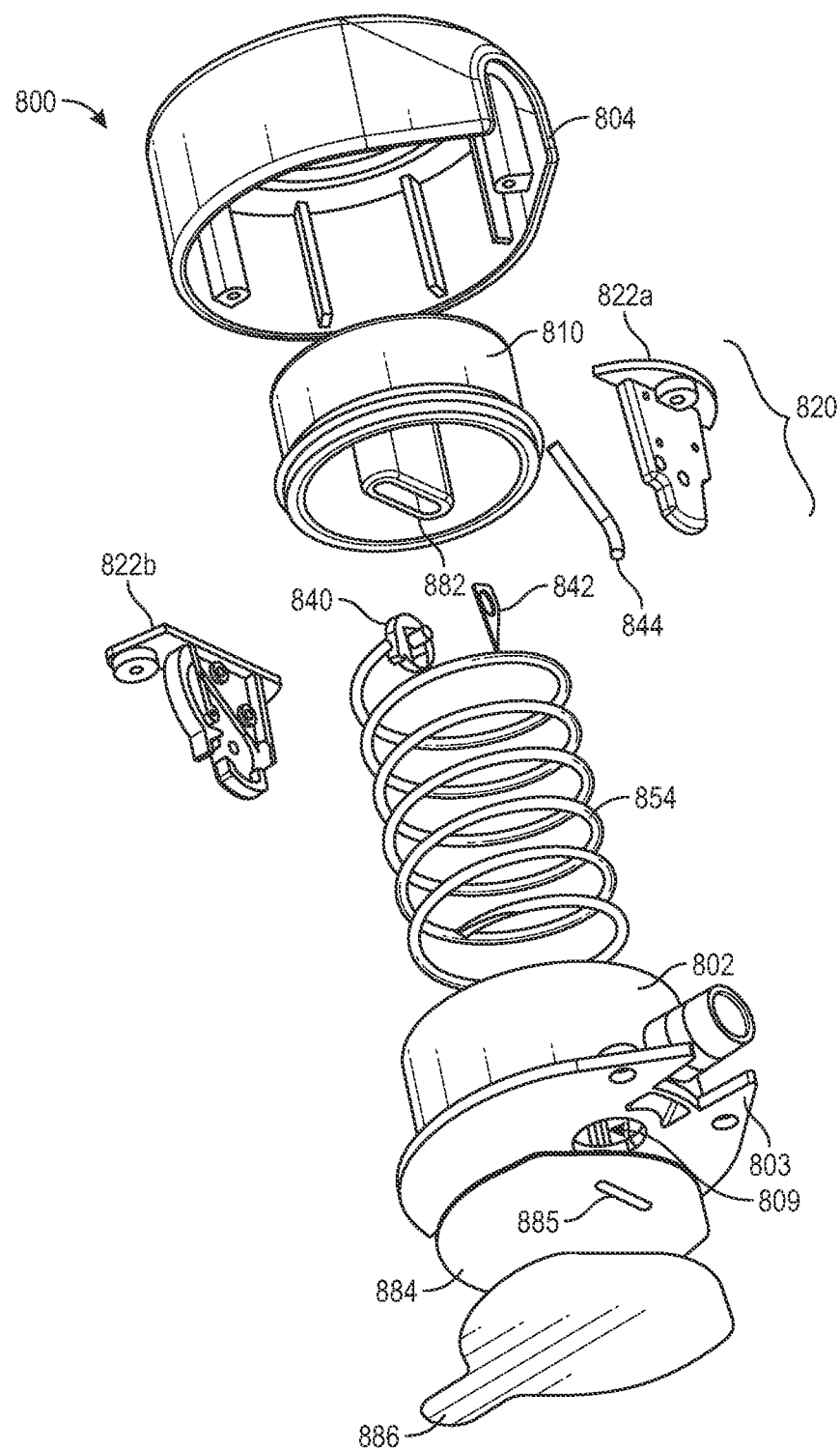

FIGS. 8A and 8B are exploded isometric views of a bodily fluid collection device 800 ("device 800") configured in accordance with additional embodiments of the present technology. The device 800 can include some features generally similar or identical to those of the device 100 described in detail above with reference to FIGS. 1A-5D, and can operate in a generally similar or identical manner. For example, referring to FIGS. 8A and 8B together, in the illustrated embodiment the device 800 includes (i) a first housing 802, (ii) a second housing 804 configured to be secured to the first housing 802, (iii) an actuator 810 movable through the first and second housings 802, 804, (iv) a skin-piercing assembly 820 coupled to the actuator 810, and (v) a retraction actuator 854. The skin-piercing assembly 820 can include a housing 822 (including an individually identified first housing portion 822a and a second housing portion 822b), a drive member 840 coupled to the housing 822 via a deployment actuator 844, and a blade 842 carried by the drive member 840. In some embodiments, the first housing portion 822a and the second housing portion 822b can be "snapped" or otherwise fastened together to secure the drive member 840, the blade 842, and the deployment actuator 844 therein. When the device 800 is applied against the skin of the subject, the actuator 810 can be depressed toward the skin of the subject to trigger the deployment actuator 844 to rotate the blade 842 to incise the skin.

In the illustrated embodiment, the first housing 802 includes a first channel portion 880 extending upward from a base 803 of the first housing 802 and extending at least partially over/around an opening 809 in the base 803. The actuator 810 can include a second channel portion 882 extending downward from the actuator 810 (e.g., a lower surface thereof). The skin-piercing assembly 820 can be positioned at least partially in the first channel portion 880 and/or the second channel portion 882. In some embodiments, the first and second channel portions 880, 882 can help guide the movement of the skin-piercing assembly 820 and can ensure that the skin-piercing assembly 820 remains aligned over the opening 809.

In the illustrated embodiment, the device 800 further includes a membrane 884 attached to the base 803 (e.g., a lower surface thereof) and spanning laterally across at least a portion of the opening 809. The membrane 884 can be bendable and/or stretchable (e.g., elastic). For example, the membrane 884 can comprise polyurethane, silicone, and/or other suitably elastic materials. The membrane 884 help facilitate a seal with the skin of a subject and, in some embodiments, can include a pre-cut opening 885 aligned with the blade 842 such that the blade 842 can extend therethrough during deployment. In other embodiments, the opening 885 can comprise a sealed but weakened or frangible line along the membrane 884. In some embodiments, the membrane 884 can be relatively thin—for example, having a thickness of less than or equal to about 250 μm, or between about 50-400 μm. In some embodiments, the membrane 884 can be of the type described in detail in U.S. patent application Ser. No. 18/571,028, filed Sep. 13, 2019, and titled "BODILY FLUID COLLECTION DEVICES AND RELATED METHODS," which is incorporated herein by reference in its entirety. In some embodiments, a liner layer 886 (e.g., a protective layer, a sanitary layer) can cover the membrane 884 prior to use, and can be removed (e.g., peeled away) by a subject prior to use.

Figure 9A:
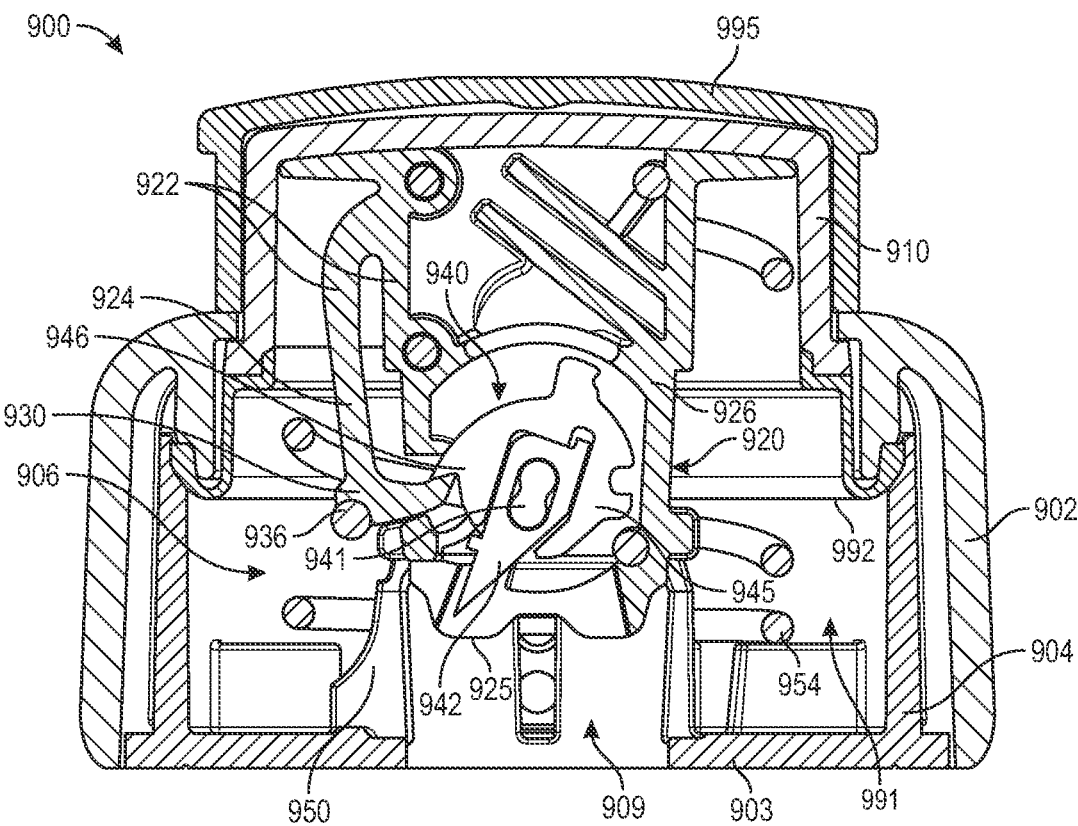
FIGS. 9A and 9B are side-cross sectional views of a bodily fluid collection device configured in accordance with additional embodiments of the present technology.
Figure 9B:
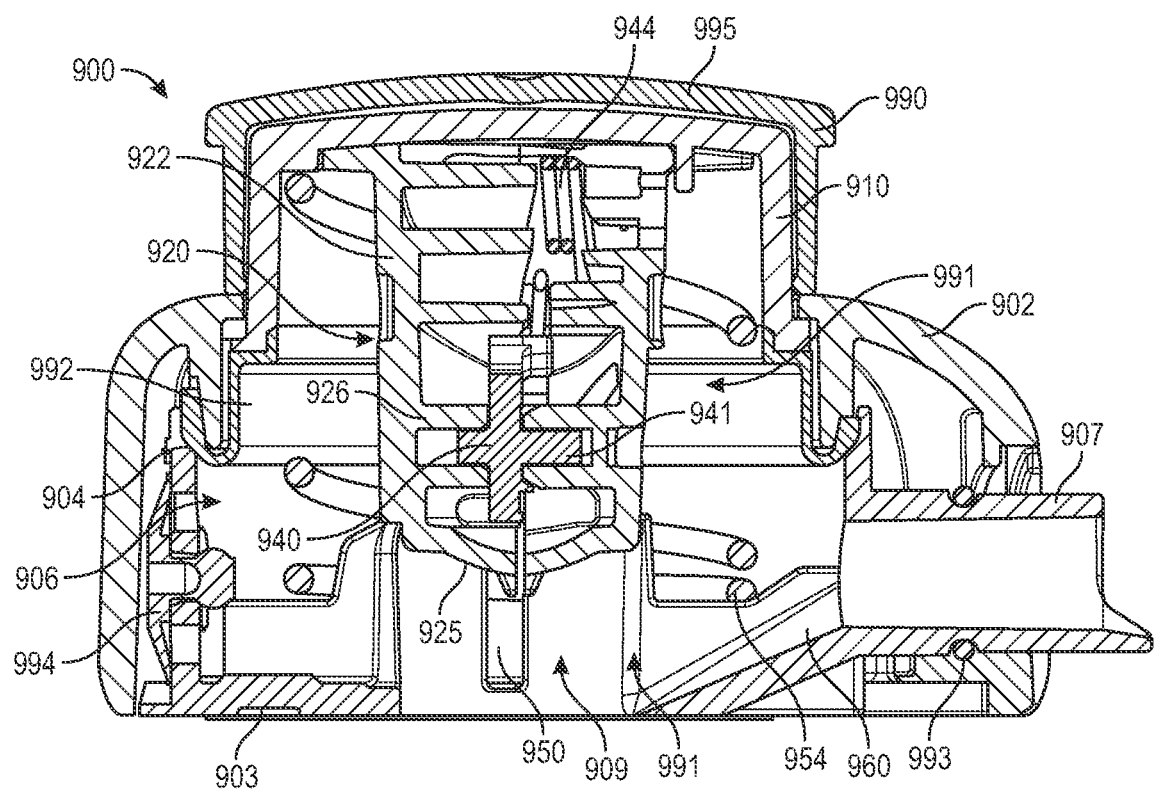
Figure 9C:
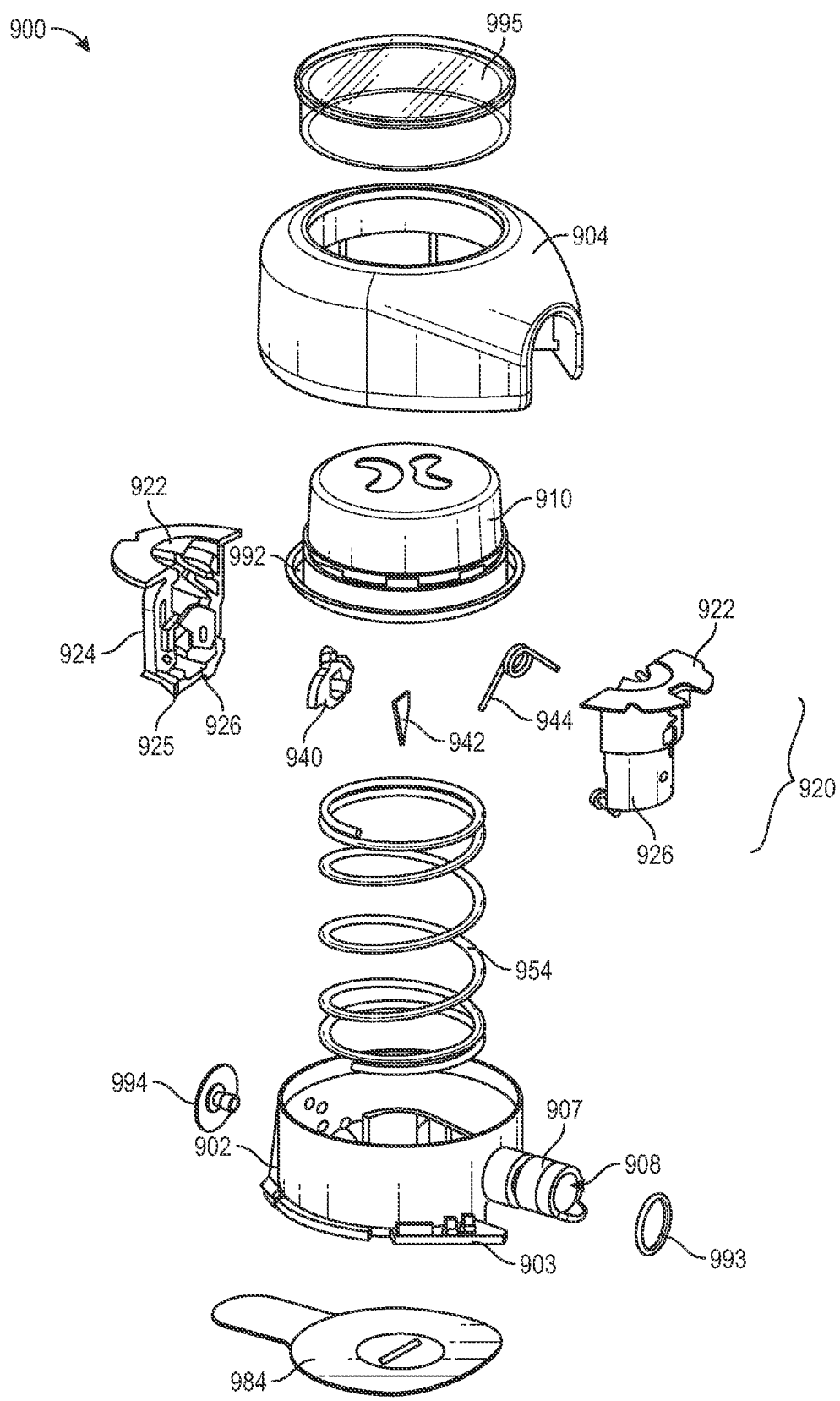
FIG. 9C is an exploded view of the device of FIGS. 9A and 9B in accordance with embodiments of the present technology.

FIGS. 9A and 9B are side-cross sectional views of a bodily fluid collection device 900 ("device 900") configured in accordance with additional embodiments of the present technology. The side cross-sectional view of FIG. 9B is rotated 90 degrees relative to the view shown in FIG. 9A. The device 900 is in a pre-deployed position in FIGS. 9A and 9B. FIG. 9C is an exploded view of the device 900. The device 900 can include some features that are at least generally similar in structure and function, or identical in structure and function, to the corresponding features of the devices 100 and/or 800 described in detail above with reference to FIGS. 1A-8, and can operate in a generally similar or identical manner to the devices 100 and/or 800.

For example, referring to FIGS. 9A-9C together, the device 900 includes a housing comprising a first (e.g., lower) housing portion 902 and a second (e.g., upper) housing portion 904 that can be secured together via, for example, an interference fit, adhesives, fasteners, and so on. The first housing portion 902 includes a base 903 and a connector 907 (FIGS. 9B and 9C). As shown in FIGS. 9A and 9B, the base 903 includes/defines an opening 909 extending therethrough and opening to an enclosed region 906. The connector 907 can define a channel 908 in fluid communication with the enclosed region 906, and is configured to be removably coupled to a collection reservoir (not shown) for receiving bodily fluid withdrawn from a subject. In some embodiments, an O-ring 993 (FIGS. 9B and 9C) or other sealing member can be positioned around the connector 907 to sealing engage the collection reservoir. The base 903 of the first housing portion 902 can define/include a fluidic channel 960 (FIG. 9B) extending from the opening 909 in the base 903 to the channel 908 in the connector 907. The device 900 further includes an actuator 910 movably coupled to and/or within the first housing portion 902 and/or the second housing portion 904, and a skin-piercing assembly 920 coupled to the actuator 910 and at least partially positioned within the enclosed region 906.

The skin-piercing assembly 920 includes a casing 922 (e.g., a cartridge) having a trigger portion 924 (e.g., a follower; obscured in FIG. 9B) and a blade holder portion 926. As best seen in FIG. 9A, the trigger portion 924 includes a first retaining feature 930 projecting toward the blade holder portion 926, and an actuation member 936. Referring again to FIGS. 9A-9C together, the blade holder portion 926 includes a shaped lower surface 925. The shaped lower surface 925 is described in further detail below with reference to FIGS. 10-11D. The skin-piercing assembly 920 is coupled to the actuator 910 and positioned over the opening 909 in the base 903 such that movement of the actuator 910 moves the skin-piercing assembly 920 through the enclosed region 906 toward/away from the opening 909. The skin-piercing assembly 920 further includes (i) a drive member 940 pivotably/rotatably mounted within the blade holder portion 926 of the casing 922, (ii) a skin-piercing feature, such as a blade 942 (obscured in FIG. 9B), coupled to the drive member 940, and (iii) a first biasing member 944 (e.g., a torsion spring; omitted in FIG. 9A for clarity) operably coupling the drive member 940 to the casing 922. Referring to FIG. 9A, the drive member 940 can include a body 945 and a second retaining feature 946 projecting from the body 945 to engage the first retaining feature 930 of the trigger portion 924 in the pre-deployed position. The actuation member 936 of the trigger portion 930 can project generally orthogonal to the drive member 940 and the blade 942.

In the pre-deployed position shown in FIGS. 9A and 9B, (i) the first biasing member 944 is biased (e.g., under load) to rotate the drive member 940 about a pivot axis 941 in a counterclockwise direction and (ii) the second retaining feature 946 abuts and engages the first retaining feature 930 to inhibit the drive member 940 (and the blade 942) from pivoting about the pivot axis 941 and to maintain the first biasing member 944 in a biased state. Referring again to FIGS. 9A-9C together, the device 900 further includes a release member 950 (obscured in FIG. 9C) coupled to the base 903 within the enclosed region 906. As described in detail below with reference to FIGS. 12A-12D, movement of the actuator 910 toward the base 903 engages the actuation member 936 of the trigger portion 924 with the release member 950 to drive/flex the first retaining feature 930 away from the second retaining feature 946 to permit the first biasing member 944 to drive the drive member 940 about the pivot axis 941 to drive the blade 942 along/past the lower surface 925 of the casing 922. The device 900 can further include a second biasing member 954 operably coupled between the actuator 910 and the first housing portion 902 and/or the second housing portion 904 and configured to bias and drive the actuator 910 and the skin-piercing assembly 920 away from the base 903.

In the illustrated embodiment, the device 900 further includes a sealing member 992 coupled between the actuator 910 and the first housing portion 902 and/or the second housing portion 904 and defining a sealed volume 991 (FIGS. 9A and 9B) over the opening 909 within the enclosed region 906. For example, in the illustrated embodiment the sealing member 992 is secured at/to an interface between the first housing portion 902 and the second housing portion 904. The device 900 can further include a valve 994 (obscured in FIG. 9A) extending through the first housing portion 902 and configured to (i) permit air to leave through the valve 994 from the sealed volume 991 to outside the device 900 and (ii) inhibit air from entering through the valve 994 from outside the device 900 to within the sealed volume 991. Accordingly, the valve 994 can be a one-way valve, such as an umbrella valve. The sealing member 992 can be a flexible membrane or member that can bend and/or is elastic. Accordingly, downward movement of the actuator 910 toward the base 903 can flex the sealing member 992 to decrease the volume of the sealed volume 991 and drive air through the valve 994 to outside the housing portion 902. Oppositely, upward movement of the actuator 910 in a direction away from the base 903 can flex the sealing member 992 to increase the volume of the sealed volume 991 while the valve 994 inhibits air from entering the sealed volume—thereby decreasing the pressure in the sealed volume 991 during use when the base 903 is sealed against the skin of the subject and a collection reservoir sealingly engages the connector 907. As described in detail above, this low pressure can act directly or indirectly against the skin of the subject to draw the skin toward/into the opening 909 to, for example, increase a blood draw volume of the device 900.

In the illustrated embodiment, the device 900 further includes a removable cap 995 positioned over the actuator 910. The cap 995 can inhibit actuation of the actuator 910 before use, and can be removed to provide access to the actuator 910 and allow use of the device 900. In some embodiments, the device 900 can further include a membrane and/or adhesive 984 (FIG. 9C) at least partially over a bottom surface of the base 903.

Figure 10:
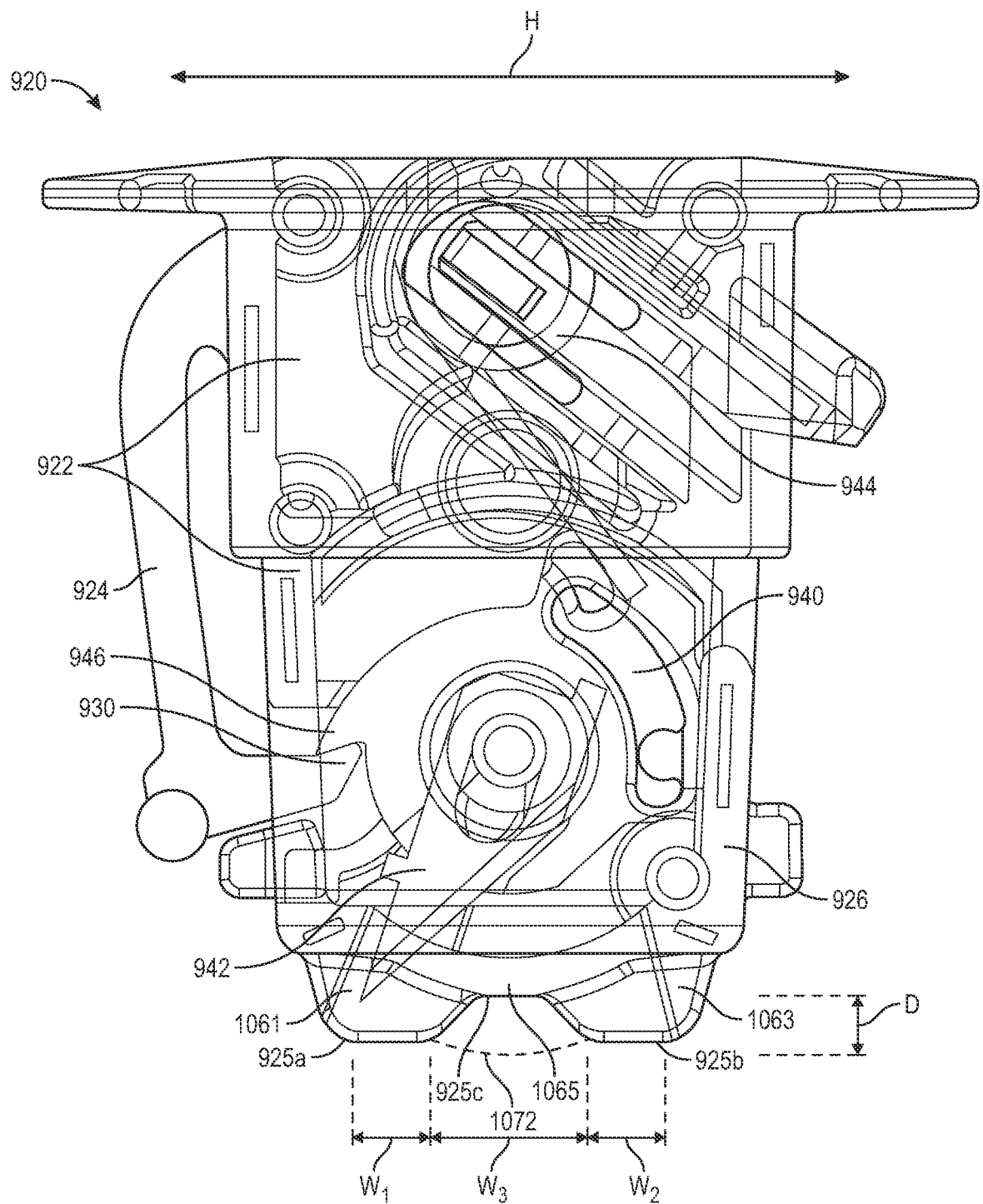
FIG. 10 is a side view of a skin-piercing assembly of the device of FIGS. 9A-9C in accordance with embodiments of the present technology.

FIG. 10 is a side view of the skin-piercing assembly 920 of the device 900 configured in accordance with embodiments of the present technology. The casing 922 is shown as partially transparent in FIG. 10 for clarity. In the illustrated embodiment, a lower portion of the blade holder portion 926 includes a first projection 1061, a second projection 1063, and a gap portion 1065 therebetween that collectively define the lower surface 925 (identified via reference numbers 925a-c). More specially, the first projection 1061, the second projection 1063, and the gap portion 1065 define a first lower surface portion 925a, a second lower surface portion 925b, and a third lower surface portion 925c, respectively. In the illustrated embodiment, the first and second lower surface portions 925a-b are each generally planar and extend substantially parallel to a horizontal axis H of the skin-piercing assembly 920 (e.g., an axis extending orthogonal to the direction the skin-piercing assembly 920 moves through the first and second housings 902, 904 toward and away the base 903 as shown in FIGS. 9A-9C). Accordingly, the first and second lower surface portions 925a-b can be referred to as flat portions and/or the like. In the illustrated embodiment, the third lower surface portion 925c curves upward away from the first and second lower surface portions 925a-b and has a generally curved-trapezoidal shape, and the first and second projections 1061, 1063 each have a generally trapezoidal or curved trapezoidal shape.

As described in detail below with reference to FIGS. 12A-12D (and discussed previously in detail with reference to FIGS. 4A-4D), depressing the actuator 910 can move the skin-piercing assembly 920 toward the base 903 such that lower surface 925 presses against and engages skin of the subject. The skin of the subject can conform to the lower surface 925 of the casing 922 such that the skin fills the gap portion 1065 and substantially contacts each of the lower surface portions 925a-c. Before actuation of the drive member 940 (e.g., when the device 900 is in the pre-deployed and partially-deployed positions), the blade 942 can be retained within the casing 922 within/adjacent to the first projection 1061. When the drive member 940 is rotated by the first biasing member 944, the blade 942 can sweep across the gap portion 1065 before being covered and retained by the second projection 1063—forming an incision 1072 within the skin of the subject. In some embodiments, the first and second projections 1061, 1063 are configured (shaped, sized, positioned) to inhibit the blade 942 from contacting the skin of the subject until the blade 942 reaches and sweeps through the gap portion 1065.

In some aspects of the present technology, the contour of the lower surface 925 is expected to improve a consistency in wound length, wound depth, blood draw, and/or another aspect of wound formation and blood withdrawal of the device 900. The first lower surface portion 925a, the second lower surface portion 925b, and the third lower surface portion 925c can have a first width $W_1$, a second width $W_2$, and a third width $W_3$, respectively. In some embodiments, the first width $W_1$ can be equal to or about the same as the second width $W_3$. In some embodiments, the first and second widths $W_1$, $W_2$ are less than the third width $W_3$. For example, the third width $W_3$ can be between about 1.1-2.5 times (e.g., about 2.0 times) greater than the first and second widths $W_1$, $W_2$. Further, the gap portion 1065 can have a depth D that, in combination with the positioning and size of the blade 942, sets/controls a maximum depth of the incision 1072 created by the blade 942.

In some embodiments, any of the first through third widths $W_1$-$W_3$ and/or the shapes of the lower surface portions 925a-c can be changed to change the shape of the corresponding incision in the skin of the subject. For example, FIGS. 11A-11D are enlarged side views of the skin-piercing assembly 920 in accordance with additional embodiments of the present technology. The casing 922 is shown as partially transparent in FIGS. 11A-11D for clarity.

Figure 11A:
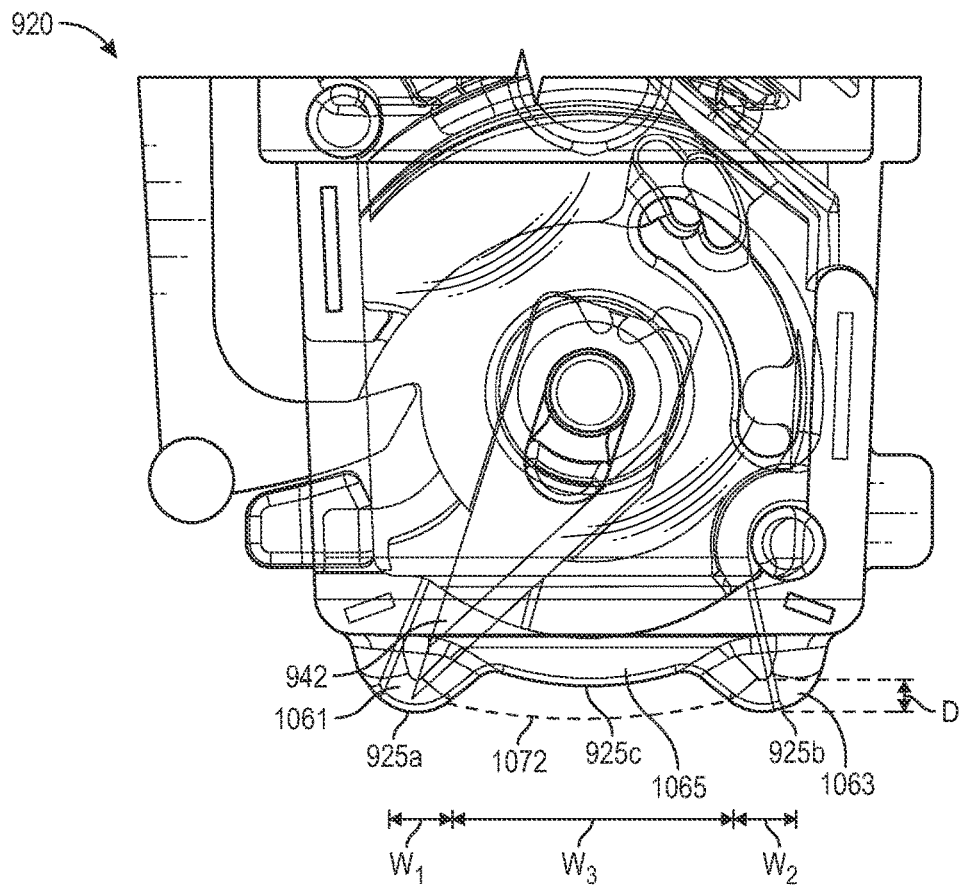
FIGS. 11A-11D are enlarged side views of the skin-piercing assembly of FIG. 10 in accordance with additional embodiments of the present technology.

Referring first to FIG. 11A, in the illustrated embodiment the first and second projections 1061, 1063 each have a more rounded shape than that shown in FIG. 10. Further, the first and second widths $W_1$, $W_2$ of the first and second surface portions 925a-b are shorter than those shown in FIG. 10 and, accordingly, the third width $W_3$ of the third surface portion 925c is relatively longer than the third width $W_3$ shown in FIG. 10. For example, the third width $W_3$ can be between about 4.0-5.0 times (e.g., about 4.5 times) greater than the first and second widths $W_1$, $W_2$. Accordingly, the gap portion 1065 can have a relatively more rectangular shape or elongated trapezoidal shape. In some embodiments, the depth D of the gap portion 1065 can be shorter than that of the gap portion 1065 shown in FIG. 10. Therefore, the resulting incision 1072 created by the blade 942 can have a relatively longer width and shorter depth.

Figure 11B:
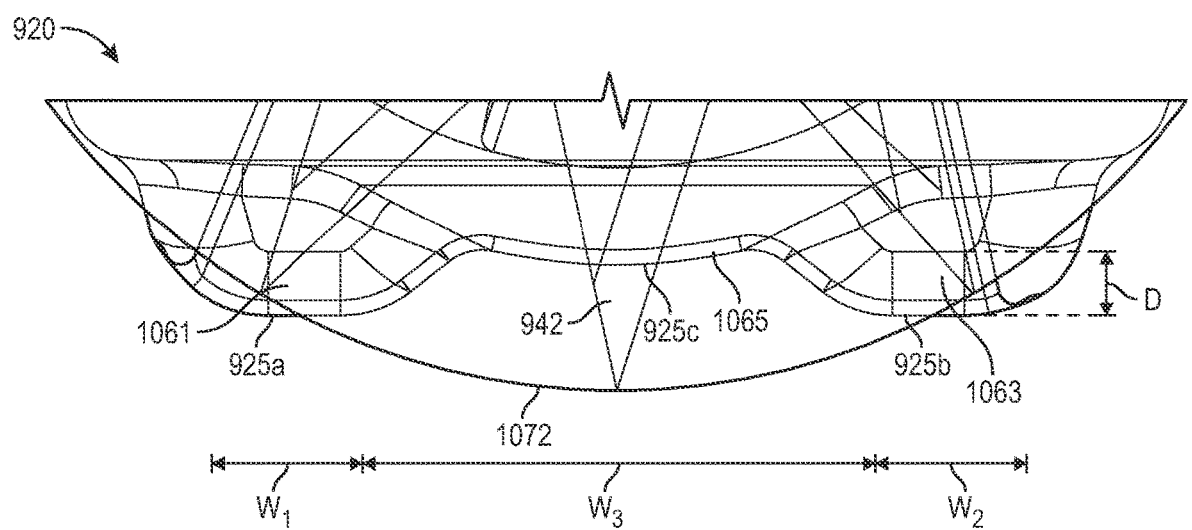

Referring next to FIG. 11B, in the illustrated embodiment the first and second projections 1061, 1063 each have a more trapezoidal shape than that shown in FIG. 11A. Further, the first and second widths $W_1$, $W_2$ of the first and second surface portions 925a-b are (i) shorter than those shown in FIG. 10 and (ii) longer than those shown in FIG. 11A. Accordingly, the third width $W_3$ of the third surface portion 925c is relatively longer than the third width $W_3$ shown in FIG. 10, but shorter than that shown in FIG. 11A. For example, the third width $W_3$ can be between about 2.5-3.5 times (e.g., about 3.1 times) greater than the first and second widths $W_1$, $W_2$. In some embodiments, the depth D of the gap portion 1065 can be shorter than that of the gap portion 1065 shown in FIG. 10 and longer that of the gap portion 1065 shown in FIG. 11A. Further, in the illustrated embodiment the first and second projections 1061, 1063 are configured (shaped, sized, positioned) such that blade 942 extends/passes by a portion of the first and second lower surfaces portions 925a-b along its arcuate cutting path before reaching and sweeping through the gap portion 1065.

Figure 11C:
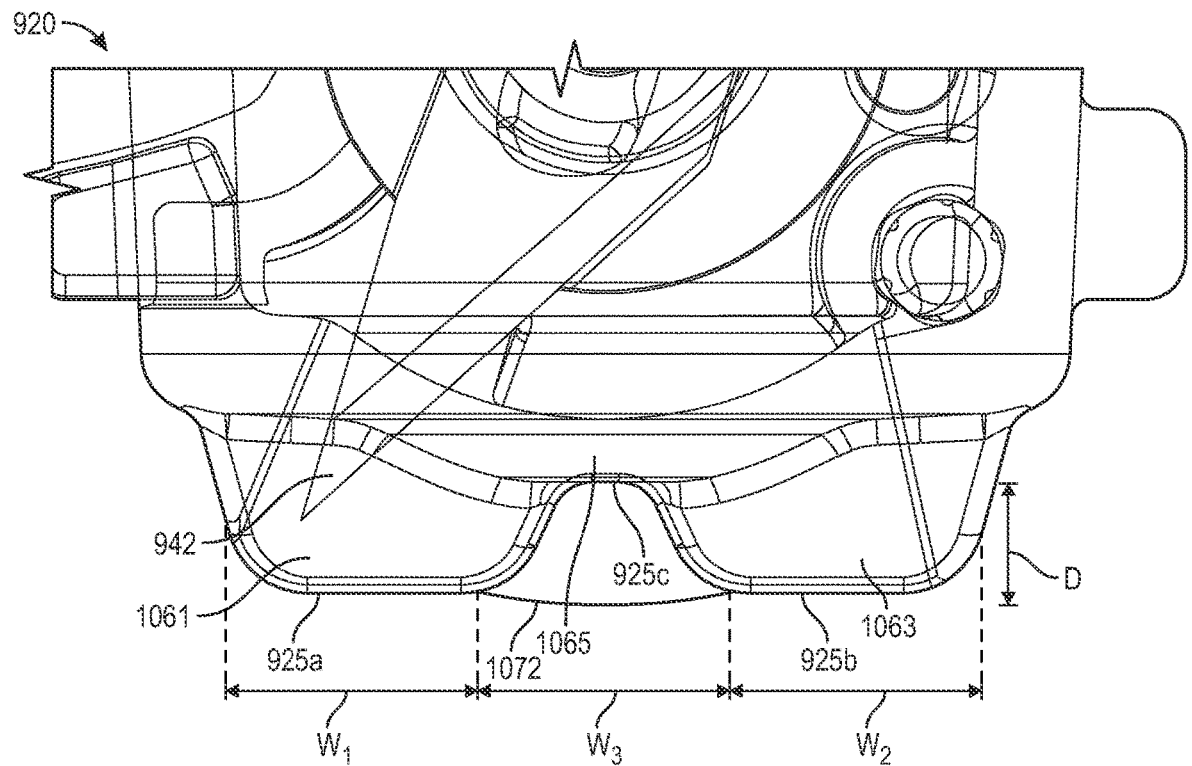
Figure 11D:
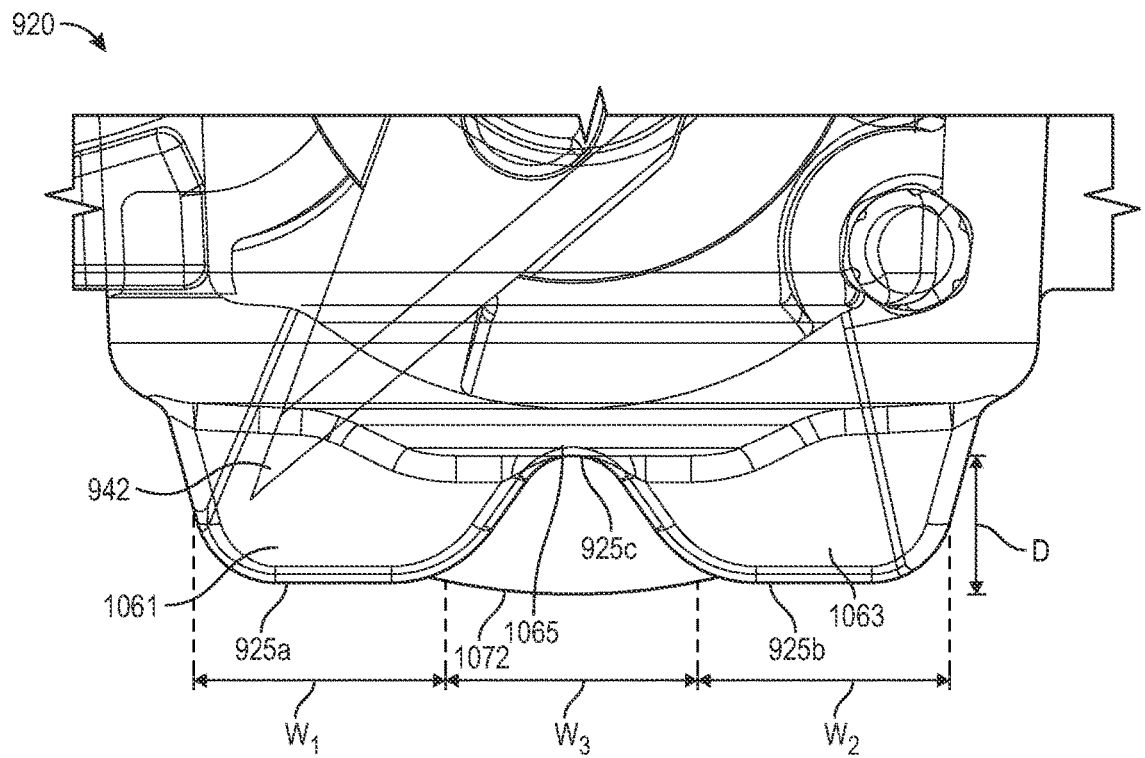

Referring next to FIG. 11C, in the illustrated embodiment the first and second widths $W_1$, $W_2$ of the first and second surface portions 925a-b, respectively, are longer than those shown in FIG. 10. Accordingly, the third width $W_3$ of the third surface portion 925c can be relatively shorter than the third width $W_3$ shown in FIG. 10. For example, the first and second widths $W_1$, $W_2$ can be between about 1.0-1.2 times (e.g., about 1.1 times) greater than the third width $W_3$. Further, in the illustrated embodiment the gap portion 1065 has a more bell-curved like shape and has a longer depth D than the gap portion 1065 shown in FIG. 10. Therefore, the resulting incision 1072 created by the blade 942 can have a relatively shorter width and deeper depth than that shown in FIG. 10.

Referring next to FIG. 11C, in the illustrated embodiment the first and second widths $W_1$, $W_2$ of the first and second surface portions 925a-b are longer than those shown in FIG. 11C. Accordingly, the third width $W_3$ of the third surface portion 925c can be relatively shorter than the third width $W_3$ shown in FIG. 11C. For example, the first and second widths $W_1$, $W_2$ can be between about 1.2-1.5 times (e.g., about 1.3 times) greater than the third width $W_3$. Further, in the illustrated embodiment the gap portion 1065 has a more bell-curved like shape and has a longer depth D than the gap portion 1065 shown in FIG. 11C. Therefore, the resulting incision 1072 created by the blade 942 can have a relatively shorter width and deeper depth than that shown in FIG. 11C.

FIGS. 12A-12D are side cross-sectional views of the device 900 of FIGS. 9A-9C at different stages of a method of withdrawing bodily fluid from a subject in accordance with embodiments of the technology. The device 900 is in the pre-deployed position in FIG. 12A, a partially-deployed position in FIG. 12B, a deployed position in FIG. 12C, and a post-deployed position in FIG. 12D.

Figure 12A:
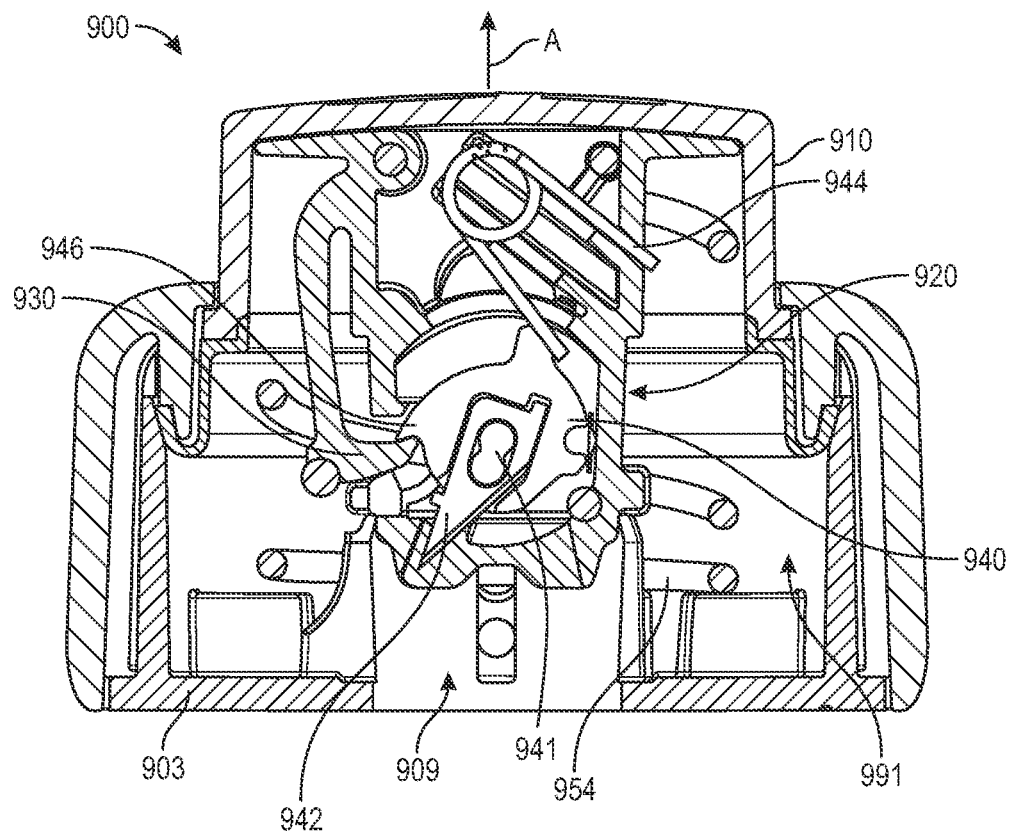
FIGS. 12A-12D are side cross-sectional views of the device of FIGS. 9A-9C and at different stages of a method of withdrawing bodily fluid from a subject in accordance with embodiments of the technology.

Referring first to FIG. 12A, the device 900 can initially be placed against the skin of a subject (not shown) in the pre-deployed position. More specifically, the base 903 can be positioned against the skin such that the opening 909 is over a portion of the skin. In some embodiments, the base 903 (e.g., a lower surface thereof) can sealingly engage the skin around the opening 909. A collection reservoir can be secured to/over the connector 907 (FIGS. 9B and 9C) before or after the device 900 is applied against the skin and can sealingly engage the connector 907. Accordingly, the sealed volume 991 can be sealed after the device 100 is applied against the skin with the collection reservoir secured to the connector 907. Further, in the pre-deployed position the second biasing member 954 biases the actuator 910—and the skin-piercing assembly 920 attached thereto—away from the opening 909 in the base 903 in the direction indicated by the arrow A (e.g., a retraction direction). Additionally, the first biasing member 944 biases the drive member 940 to rotate in the counterclockwise direction. However, the engagement of the first and second retaining features 930, 946 inhibits the drive member 940 (and the blade 942) from pivoting about the pivot axis 941. Accordingly, the skin-piercing assembly 920 is in a loaded or ready-to-fire state.

Figure 12B:
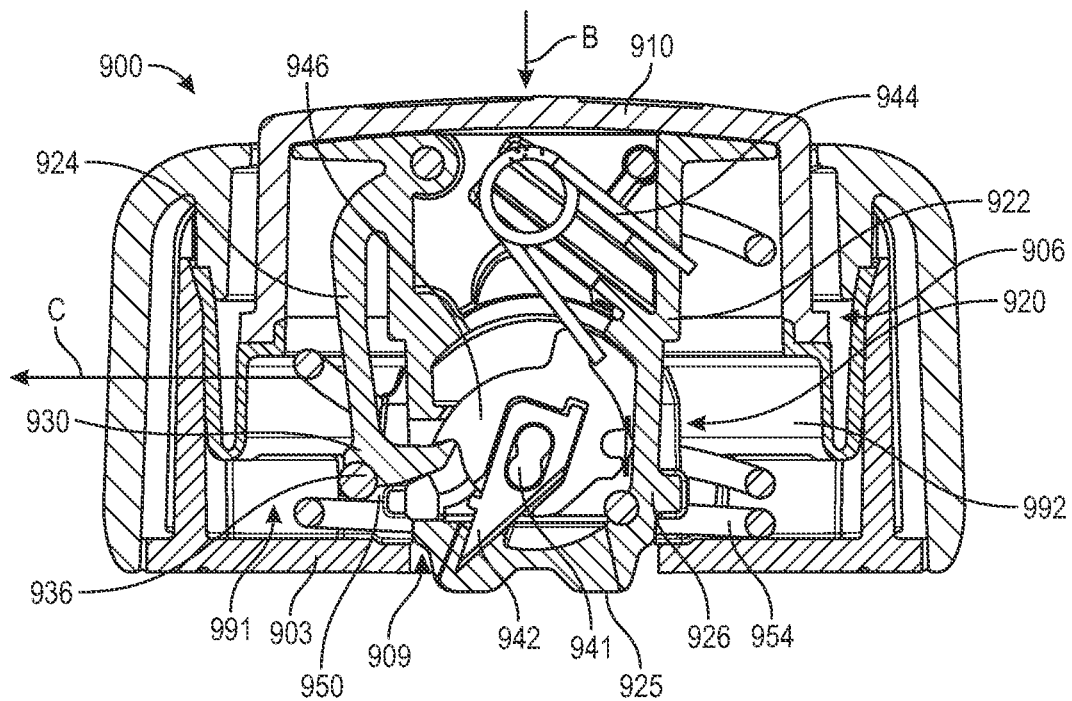

Referring next to FIG. 12B, the device 900 can be moved from the pre-deployed position to the partially deployed position by moving (e.g., pressing by the subject or another) the actuator 910 toward the base 903 in the direction indicated by the arrow B (e.g., a deployment direction). Moving the actuator 910 moves the skin-piercing assembly 920 through the enclosed region 906 and at least partially through the opening 909 in the base 903. More specifically, in some embodiments the lower surface 925 of the blade portion 926 of the casing 922 can extend at least partially through the opening 909 to contact the skin 970 of the subject. As described in detail above with reference to FIGS. 10-11D, the contoured lower surface 925 can depress the skin of the subject such that the skin conforms to the shape of the lower surface 925. Moreover, in the partially-deployed position, the retaining feature 930 still engages the second retaining feature 946 to inhibit the drive member 940 (and the blade 942) from pivoting about the pivot axis 941. In some embodiments, the actuation member 936 can slightly contact the release member 950 such that the trigger portion 924 is slightly flexed outward away from the blade portion 926 and the drive member 940 in the direction of arrow C. Movement of the actuator 910 in the direction indicated by the arrow B also compresses the sealing member 992, thereby reducing the volume of the sealed volume 991 and driving air out of sealed volume 991 through the valve 994 (FIGS. 9B and 9C).

Figure 12C:
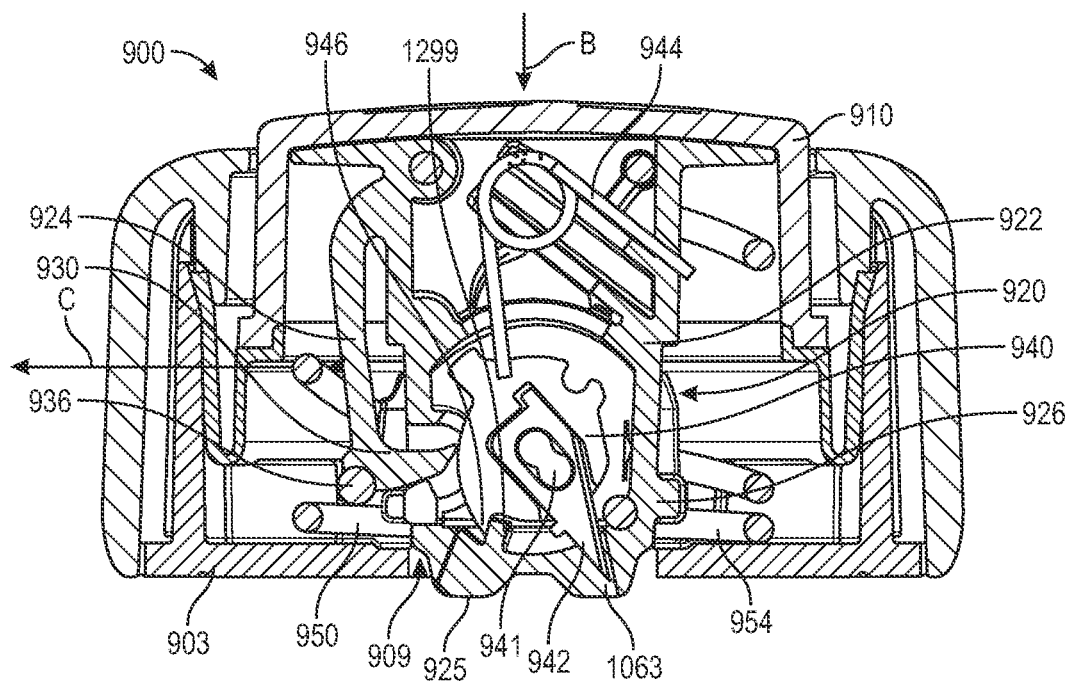

Referring next to FIG. 12C, the device 900 can be moved from the partially-deployed position to the deployed position by continuing to move the actuator 910 toward the base 903 in the direction indicated by arrow B. Continuing to move the actuator 910 moves the first retaining feature 930 of the trigger portion 924 into engagement with the release member 2950 such that the first retaining feature 930 flexes away from and out of engagement with the second retaining feature 946 as indicated by the arrow C. The trigger portion 924 can flex enough to release/disengage the second retaining feature 946 from the first retaining feature 930. When the second retaining feature 946 disengages the first retaining feature 930, the first biasing member 944 is configured to move from a biased stated to an at least partially relaxed state to thereby drive the drive member 940 to pivot about the pivot axis 941. As the drive member 940 pivots, the drive member 940 simultaneously moves (e.g., sweeps) the blade 942 along an arcuate path through and across at least a portion of the opening 909 past the lower surface 925 of the casing to form an incision in the skin of the subject. The shape of the resulting incision can be determined by the shape of the contoured lower surface 925, as described in detail above with reference to FIGS. 10-11D. After deployment, the blade 942 can be fully positioned within the casing 922 (e.g., with a tip of the blade 942 covered by the second projection 1063). In some embodiments, the blade portion 926 includes a stop feature 1299 configured to engage the second retaining feature 946 and inhibit further movement of the drive member 940 and the blade 942.

Figure 12D:
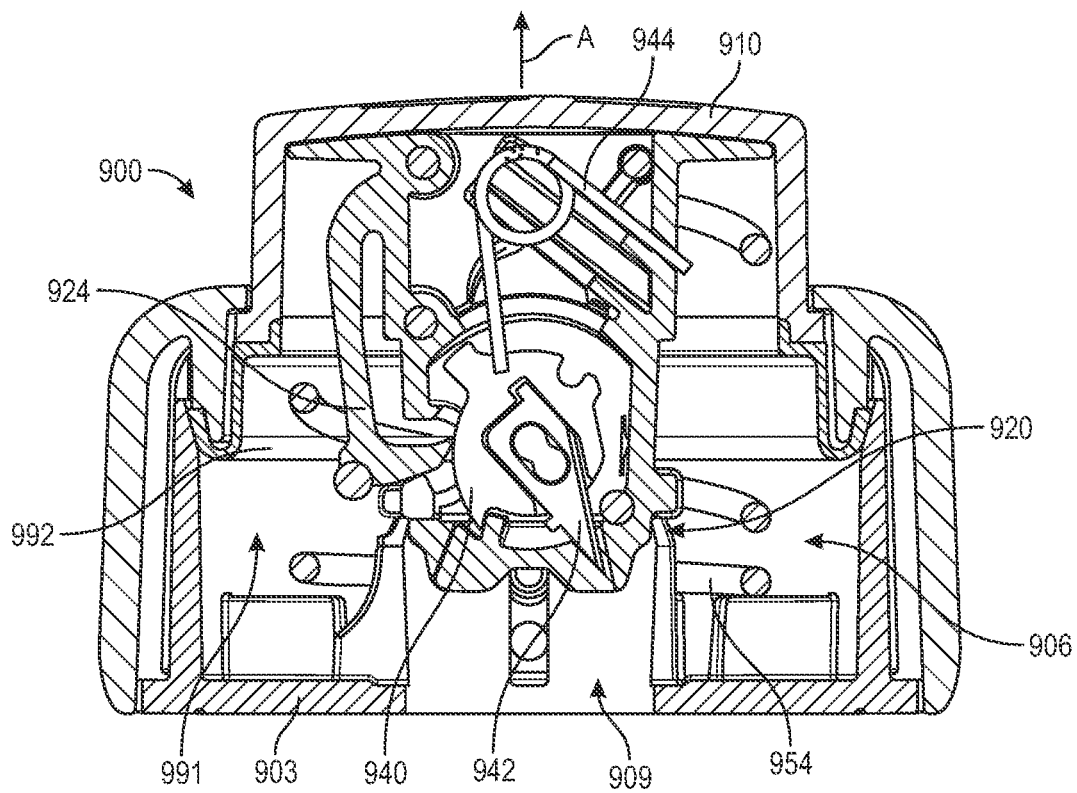

Referring next to FIGS. 12D, the device 900 can be moved from the deployed position to the post-deployed position by releasing the actuator 910 to allow the second biasing member 954 to drive the actuator 910 and the skin-piercing assembly 920 away from the base 903 in the direction indicated by the arrow A. The retraction of the actuator 910 can move the skin-piercing assembly 920 out of contact within the skin of the subject and fully into the enclosed region 906. In some embodiments, with reference to FIGS. 12A and 12D together, the second biasing member 954 can return the actuator 910 to the pre-actuated position. Nevertheless, the device 900 can be configured as a single-use device that cannot be redeployed. For example, in the illustrated embodiment the device 900 is configured such that subsequent actuation of the actuator 910 when the device 900 is in the post-deployed configuration does not pivot the blade 942 into the opening 909. Specifically, the first biasing member 944 is no longer biased in the post-deployed configuration (e.g., after the drive member 940 is released from the trigger portion 924) and therefore cannot drive the blade 942 through the opening 909.

Further, retraction of the actuator 910 in the direction of the arrow B drives the sealing member 992 to expand upward with the actuator 910 to increase the volume of the sealed volume 991. At the same time, the valve 994 (FIGS. 9B and 9C) inhibits air from entering from outside the device 900 into the sealed volume 991. Accordingly, the expansion/movement of the sealing member 992 decreases the pressure in the sealed volume 991 to generate negative/vacuum pressure within the sealed volume 991. With reference to FIGS. 9A-9B and 12A-12D together, in some aspects of the present technology the vacuum pressure can help draw a bodily fluid (e.g., blood) at least partially (i) from the incision in the skin of the subject, (ii) through the opening 909 into the enclosed region 906, (iii) along the fluidic channel 960, (iv) into the channel 908, and/or (v) into a collection reservoir coupled to the connector 907.

Figure 13B:
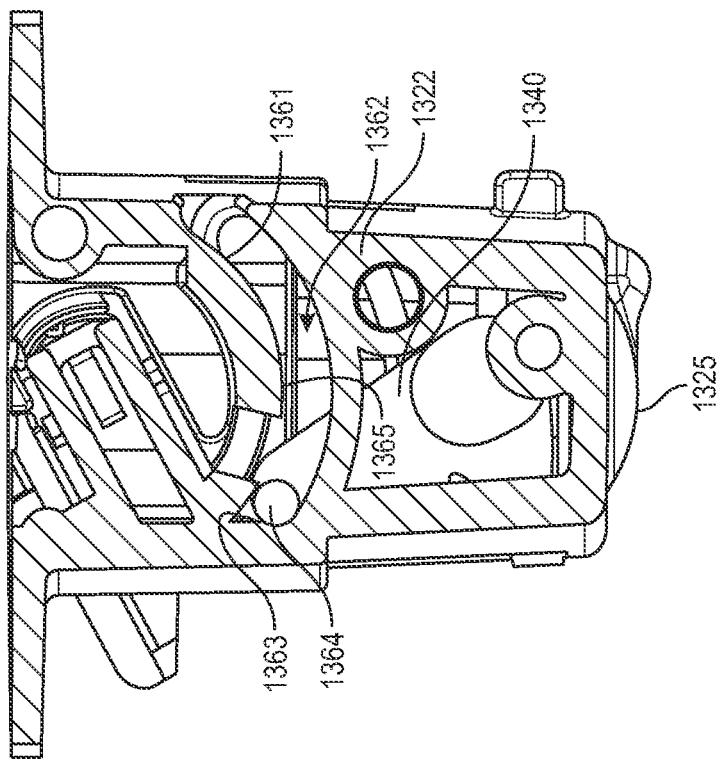
FIGS. 13A and 13B are a side cross-sectional view and a side view, respectively, of a skin-piercing assembly configured in accordance with additional embodiments of the present technology.
Figure 13A:
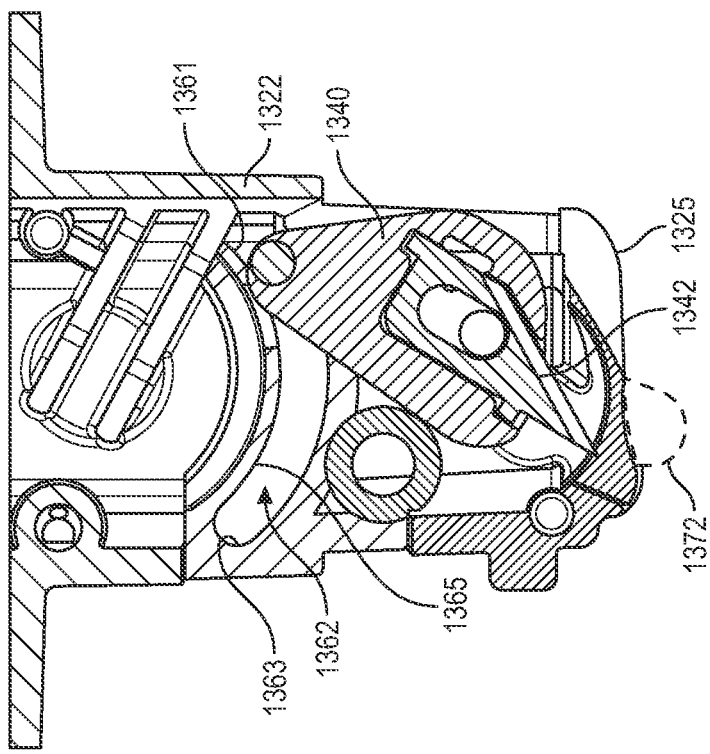

In other embodiments, bodily fluid collection devices configured in accordance with the present technology can have (i) skin-piercing assemblies that drive a blade or other skin-piercing feature through an opening in other manners and/or (ii) additional features for controlling the length and/or depth of an incision. FIGS. 13A and 13B, for example, are a side cross-sectional view and a side-view, respectively, of a skin-piercing assembly 1320 configured in accordance with additional embodiments of the present technology. The skin-piercing assembly 1320 is in a pre-deployed position in FIG. 13A and a deployed position in FIG. 13B. The skin-piercing assembly 1320 can (i) be incorporated into one or more of the devices 100, 800, and/or 900 described in detail above with reference to FIGS. 1A-12D. Likewise, the skin-piercing assembly 1320 can include some features that are at least generally similar in structure and function, or identical in structure and function, to the corresponding features of the skin-piercing assemblies 120, 620, and/or 920 described in detail above with reference to FIGS. 1A-12D, and can operate in a generally similar or identical manner to the skin-piercing assemblies 120, 620, and/or 920.

For example, referring to FIGS. 13A and 13B together, in the illustrated embodiment the skin-piercing assembly 1320 includes a casing 1322 including a lower surface 1325 and that contains a drive member 1340 movably mounted therein. A blade 1342 is coupled to the drive member 1340, and a biasing member (not shown) can operably couple the drive member 1340 to the casing 1322. The biasing member is configured to drive the blade 1342 past the lower surface 1325 into the skin of a subject as described in detail above.

In the illustrated embodiment, the drive member 1340 includes a projection 1364 and the casing 1322 includes/defines a track 1362 (e.g., an opening, channel, elongate path). The projection 1364 extends at last partially into the track 1362 such that the projection 1364 is confined to move along the track 1362. The track 1362 can extend between a first end portion 1361 and a second end portion 1363 and can have a length and shape (e.g., a varying elevation) selected to correspond to a desired path of the blade 1342 and a corresponding size (e.g., length, depth) of an incision 1372 (FIG. 13A) created by the blade 1326. In the illustrated embodiment, the track 1362 curves downward between the first and second end portions 1361, 1363.

When the drive member 1340 is actuated, the biasing member (not shown) can drive the drive member along the track 1362 from the first end portion 1361 toward the second end portion 1363. The path of the blade 1342 is controlled/defined by the configuration (e.g., shape, size, length) of the track 1362 to deploy the blade 1326 past the lower surface 1325 into the skin of a subject to create the incision 1372. More specifically, in the illustrated embodiment the skin-piercing assembly 1320 moves laterally from the first end portion 1361 toward the second end portion 1363 while rotating to deploy the blade 1326 past the lower surface 1325 as the projection 1364 passes along a middle portion 1365 of the track 1362. In some embodiments, the configuration (e.g., shape, size) of the middle portion 1365 and the lower surface 1325 can control a depth and/or shape of an incision created by the blade 1326. In some aspects of the present technology, the incision 1372 can have a similar shape as any of the incisions 1072 described in detail above with reference to FIGS. 10-11D.

The following examples are illustrative of several embodiments of the present technology:

1. A device for withdrawing bodily fluid from a subject, the device comprising:
   a housing including a base and a release member extending from the base, wherein the base has an opening extending therethrough;
   a skin-piercing assembly positioned at least partially within the housing, wherein the skin-piercing assembly includes—
      a trigger portion and a blade holder portion;
      a drive member pivotably coupled to the blade holder portion;
      a blade carried by the drive member; and
      a biasing member operably coupled to the drive member; and
   an actuator operably coupled to the skin-piercing assembly and movable from a first position to a second position relative to the housing, wherein—
      in the first position, the drive member is configured to engage the trigger portion to maintain the biasing member in a biased configuration, and
      movement of the actuator from the first position to the second position is configured to engage the trigger portion with the release member to disengage the trigger portion from the drive member to permit the biasing member to drive the blade at least partially through the opening in the base.

2. The device of example 1 wherein the movement of the actuator from the first position to the second position is configured to engage the trigger portion with the release member to deflect the trigger portion away from the blade holder portion.

3. The device of example 1 or example 2 wherein the blade holder portion includes a lower surface configured to extend at least partially through the opening in the base when the actuator is in the second position.

4. The device of example 3 wherein the blade holder includes a first projection, a second projection, and a gap portion between the first and second projections, and wherein the first projection, the second projection, and the gap portion define the lower surface of the blade holder.

5. The device of example 4 wherein the first and second projections each include a generally planar lower surface.

6. The device of example 5 wherein the gap portion has a generally curved-trapezoidal shape.

7. The device of example 5 wherein the gap portion has a generally bell-curved shape.

8. The device of any one of examples 5-7 wherein a width of the first projection and a width of the second projection are greater than a width of the gap portion.

9. The device of any one of examples 5-7 wherein a width of the first projection and a width of the second projection are smaller than a width of the gap portion.

10. The device of any one of examples 1-9, further comprising:
- a flexible sealing member positioned within the housing and defining a sealed volume within the housing over the opening in the base; and
- a one-way valve coupled to the housing and configured to (a) inhibit air from entering the sealed volume from outside the device and (ii) permit air to exit the sealed volume to outside the device.

11. A device for withdrawing bodily fluid from a subject, the device comprising:
- a housing including a base having an opening extending therethrough, wherein the base is configured to be positioned adjacent skin of the subject; and
- a skin-piercing assembly positioned at least partially within the housing, wherein the skin-piercing assembly includes—
  - a casing having a lower surface;
  - a blade pivotably coupled to the casing; and
  - a biasing member operably coupled to the blade and configured to drive the blade relative to the lower surface; and
- an actuator operably coupled to the skin-piercing assembly and movable relative to the housing, wherein—
  - the actuator is movable to a first position to drive the lower surface of the casing at least partially through the opening in the base and into contact with the skin; and
  - the actuator is movable to a second position to release the biasing member to permit the biasing member to drive the blade along a path through the skin and relative to the lower surface of the casing.

12. The device of example 11 wherein the lower surface of the casing has a curved shape.

13. The device of example 11 or example 12 wherein the lower surface of the casing has a shape that matches the path of the blade such that the blade extends through the skin at a generally uniform depth along the path.

14. The device of any one of examples 11-13 wherein the casing includes a first projection, a second projection, and a gap portion between the first and second projections, and wherein the first projection, the second projection, and the gap portion define the lower surface of the blade holder.

15. The device of example 14 wherein the first and second projections each include a generally planar lower surface.

16. The device of example 15 wherein the gap portion has a generally curved-trapezoidal shape.

17. The device of example 15 wherein the gap portion has a generally bell-curved shape.

18. The device of any one of examples 15-17 wherein a width of the first projection and a width of the second projection are greater than a width of the gap portion.

19. A skin-piercing assembly, comprising:
- a casing including a trigger portion and a blade holder portion, wherein the trigger portion is at least partially spaced apart from the blade holder portion, wherein the trigger portion includes a first retaining feature, and wherein the blade holder portion includes a lower surface;
- a drive member pivotably coupled to the blade holder portion of the casing, wherein the drive member includes a second retaining feature;
- a blade carried by the drive member; and
- a biasing member operably coupled between the drive member and the casing, wherein—
  - in a pre-deployed position, the second retaining feature is configured to engage the first retaining feature to maintain the biasing member in a loaded configuration; and
  - in a deployed position, the second retaining feature is configured to disengage the first retaining feature to permit the biasing member to pivot the blade at least partially past the lower surface of the casing.

20. The skin-piercing assembly of example 19 wherein the blade portion of the casing includes a first projection, a second projection, and a gap portion between the first and second projections, wherein the first projection, the second projection, and the gap portion define the lower surface of the blade holder, and wherein the first and second projections each include a generally planar lower surface.

21. A device for withdrawing bodily fluid from a subject, the device comprising:
- a housing having a sidewall and a connector extending from the sidewall;
- an actuator movable relative to the sidewall of the housing, wherein the housing and the actuator at least partially define an enclosed region, and wherein the connector includes a channel in fluid communication with the enclosed region;
- a sealing member coupled to the actuator and configured to seal an interface between the actuator and the sidewall of the housing, wherein—
  - movement of the actuator in a first direction decreases a volume of the enclosed region and advances the sealing member at least partially past the channel in the connector to permit a pressure in the enclosed region to equalize via a fluid path extending (a) from the enclosed region, (b) through the channel past the sealing member, and (c) between the actuator and the sidewall to outside the housing; and
  - movement of the actuator in a second direction, opposite the first direction, increases the volume of the enclosed region and advances the sealing member along the sidewall above the channel to reduce the pressure in the enclosed region.

22. The device of example 21, further comprising a retraction actuator operably coupled between the housing and the actuator and configured to drive the actuator in the second direction.

23. The device of example 22 wherein movement of the actuator in the first direction increases a load on the retraction actuator.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for withdrawing bodily fluid from a subject, the device comprising:
    a housing including a base and a release member extending from the base, wherein the base has an opening extending therethrough;
    a skin-piercing assembly positioned at least partially within the housing, wherein the skin-piercing assembly includes—
        a trigger portion and a blade holder portion, wherein the blade holder portion includes a lower surface;
        a drive member pivotably coupled to the blade holder portion;
        a blade carried by the drive member; and
        a biasing member operably coupled to the drive member; and
    an actuator operably coupled to the skin-piercing assembly and movable from a first position to a second position relative to the housing, wherein—
        in the first position, the drive member is configured to engage the trigger portion to maintain the biasing member in a biased configuration, and
        movement of the actuator from the first position to the second position is configured to engage the trigger portion with the release member to disengage the trigger portion from the drive member to permit the biasing member to drive the blade at least partially through the opening in the base, wherein the lower surface of the blade holder portion is configured to extend at least partially through the opening in the base when the actuator is in the second position.

2. The device of claim 1 wherein the movement of the actuator from the first position to the second position is configured to engage the trigger portion with the release member to deflect the trigger portion away from the blade holder portion.

3. The device of claim 1 wherein the blade holder portion includes a first projection, a second projection, and a gap portion between the first and second projections, and wherein the first projection, the second projection, and the gap portion define the lower surface of the blade holder portion.

4. The device of claim 3 wherein the first and second projections each include a planar lower surface region.

5. The device of claim 4 wherein the gap portion has a curved-trapezoidal shape.

6. The device of claim 4 wherein the gap portion has a bell-curved shape.

7. The device of claim 4 wherein a width of the first projection and a width of the second projection are greater than a width of the gap portion.

8. The device of claim 4 wherein a width of the first projection and a width of the second projection are smaller than a width of the gap portion.

9. A device for withdrawing bodily fluid from a subject, the device comprising:
    a housing including a base and a release member extending from the base, wherein the base has an opening extending therethrough;
    a skin-piercing assembly positioned at least partially within the housing, wherein the skin-piercing assembly includes—
        a trigger portion and a blade holder portion;
        a drive member pivotably coupled to the blade holder portion;
        a blade carried by the drive member; and
        a biasing member operably coupled to the drive member;
    a flexible sealing member positioned within the housing and defining a sealed volume within the housing over the opening in the base;
    a one-way valve coupled to the housing and configured to (a) inhibit air from entering the sealed volume from outside the device and (ii) permit air to exit the sealed volume to outside the device; and
    an actuator operably coupled to the skin-piercing assembly and movable from a first position to a second position relative to the housing, wherein—
        in the first position, the drive member is configured to engage the trigger portion to maintain the biasing member in a biased configuration, and
        movement of the actuator from the first position to the second position is configured to engage the trigger portion with the release member to disengage the trigger portion from the drive member to permit the biasing member to drive the blade at least partially through the opening in the base.

10. A device for withdrawing bodily fluid from a subject, the device comprising:
    a housing including a base having an opening extending therethrough, wherein the base is configured to be positioned adjacent skin of the subject; and
    a skin-piercing assembly positioned at least partially within the housing, wherein the skin-piercing assembly includes—
        a casing having a lower surface;
        a blade pivotably coupled to the casing; and
        a biasing member operably coupled to the blade and configured to drive the blade relative to the lower surface; and
    an actuator operably coupled to the skin-piercing assembly and movable relative to the housing, wherein—
        the actuator is movable to a first position to drive the lower surface of the casing at least partially through the opening in the base and into contact with the skin; and
        the actuator is movable to a second position to release the biasing member to permit the biasing member to drive the blade along a path through the skin and relative to the lower surface of the casing.

11. The device of claim 10 wherein the lower surface of the casing has a curved shape.

12. The device of claim 10 wherein the lower surface of the casing has a shape that matches the path of the blade such that the blade extends through the skin at a generally uniform depth along the path.

13. The device of claim 10 wherein the casing includes a first projection, a second projection, and a gap portion between the first and second projections, and wherein the first projection, the second projection, and the gap portion define the lower surface of the casing.

14. The device of claim 13 wherein the first and second projections each include a planar lower surface.

15. The device of claim 14 wherein the gap portion has a curved-trapezoidal shape.

16. The device of claim 14 wherein the gap portion has a bell-curved shape.

17. The device of claim 14 wherein a width of the first projection and a width of the second projection are greater than a width of the gap portion.

* * * * *